US012612591B2

(12) United States Patent (10) Patent No.: US 12,612,591 B2
Oudshoorn et al. (45) **Date of Patent: \*Apr. 28, 2026**

(54) INTEGRATED SYSTEM FOR BIOCATALYTICALLY PRODUCING AND RECOVERING AN ORGANIC SUBSTANCE

(71) Applicant: DELFT ADVANCED BIOFUELS B.V., Delft (NL)

(72) Inventors: Arjan Oudshoorn, Voorburg (NL); Kirsten Johanna Josephine Steinbusch, Leidschendam (NL); Robbie Wouter Hendrikus Kerste, Lage Zwaluwe (NL); David James Relph Woolner, London (GB)

(73) Assignee: DELFT ADVANCED BIOFUELS B.V., Delft (NL)

( * ) Notice: Subject to any disclaimer, the term of this patent is extended or adjusted under 35 U.S.C. 154(b) by 1013 days.

This patent is subject to a terminal disclaimer.

(21) Appl. No.: 17/627,797

(22) PCT Filed: Jun. 26, 2020

(86) PCT No.: PCT/NL2020/050421
§ 371 (c)(1),
(2) Date: Jan. 17, 2022

(87) PCT Pub. No.: WO2021/010822
PCT Pub. Date: Jan. 21, 2021

(65) Prior Publication Data
US 2022/0275323 A1 Sep. 1, 2022

(30) Foreign Application Priority Data

Jul. 18, 2019 (EP) ..................................... 19187100

(51) Int. Cl.
| *C12M 1/00* | (2006.01) |
| *C12M 1/04* | (2006.01) |
| *C12P 5/00* | (2006.01) |
| *C12P 7/06* | (2006.01) |
| *C12P 7/16* | (2006.01) |

(52) U.S. Cl.
CPC ............ *C12M 47/10* (2013.01); *C12M 27/04* (2013.01); *C12M 29/08* (2013.01); *C12P 5/007* (2013.01); *C12P 7/06* (2013.01); *C12P 7/16* (2013.01)

(58) Field of Classification Search
None
See application file for complete search history.

(56) References Cited

U.S. PATENT DOCUMENTS

| 2,320,738 A | 6/1943 | Jenkins |
| 4,368,056 A | 1/1983 | Pierce et al. |
| 5,628,906 A * | 5/1997 | Shinnar ..................... C12P 1/00 |
| | | 210/259 |
| 2003/0111410 A1 | 6/2003 | Branson et al. |
| 2011/0045581 A1* | 2/2011 | Collao Olivares .... C12M 41/24 |
| | | 435/293.1 |
| 2018/0119083 A1* | 5/2018 | Zheng .................. B01J 19/0066 |

FOREIGN PATENT DOCUMENTS

| CA | 2631138 A1 | 6/2007 |
| CN | 102732416 A | 10/2012 |
| EP | 1728846 A1 | 6/2006 |
| EP | 2196539 A1 | 6/2010 |
| ES | 2273594 A1 | 1/2007 |
| JP | 2007159582 A | 6/2007 |
| JP | 2017512062 A | 5/2017 |
| WO | 2015130167 A1 | 9/2015 |
| WO | 2017220957 A1 | 12/2017 |

OTHER PUBLICATIONS

EP Search Report for corresponding application serial No. 08787667. 8; date of filing Aug. 7, 2008; pp. 1-9.
Ladygina, N. et al. A review on microbial synthesis of hydrocarbons. Process Biochemistry. Oct. 5, 2006. vol. 41, n 5, pp. 1001-1014. ISSN 1359-5113.
Kalscheuer, R. et al. Microdiesel: *Escherichia coli* engineered for fuel production. Microbiology. Jan. 1, 2006. vol. 152, pp. 2529-2536. ISSN 1350-0872.
International Search Report for corresponding PCT Application No. PCT/NL2020/050421, mailed Sep. 18, 2020.
Littlejohns, J. (2009). "A two-phase partitioning airlift bioreactor for the treatment of BTEX contaminated gases." Biotechnology and Bioengineering, vol. 103(6), pp. 1077-1086. doi:10.1002/bit.22343.
Maass, Sebastian, (2012) "Automated drop detection using image analysis for online particle size monitoring in multiphase systems", Computers in Chemical Engineering, 21 pages.
Bednarz, Andreas, (2018) "Aerated extraction columns for in situ separation of bio-based diamines from cell suspensions." Journal of Chemical Technology & Biotechnology. doi:10.1002/jctb.5786.

* cited by examiner

*Primary Examiner* — Christian L Fronda
(74) *Attorney, Agent, or Firm* — Tarolli, Sundheim, Covell & Tummino LLP

(57) ABSTRACT

The invention relates to a method for recovering a biocatalytically produced organic substance from a reaction mixture, comprising—providing a reaction mixture, wherein the organic substance is produced using a biocatalyst, which reaction mixture comprises a substrate for the biocatalyst in a continuous aqueous phase, and wherein further a product recovery phase is present into which the organic substance migrates or onto which the organic substance absorbs or adsorbs; and—separating the product recovery phase comprising the produced substance from the aqueous phase and the biocatalyst. The invention further relates to a bioreactor system for biocatalytically producing a substance, comprising an apparatus, said apparatus comprising a reaction compartment (11) situated in a lower part of the apparatus and a separator compartment (9).

24 Claims, 15 Drawing Sheets

INTEGRATED SYSTEM FOR BIOCATALYTICALLY PRODUCING AND RECOVERING AN ORGANIC SUBSTANCE

RELATED APPLICATIONS

The present invention is a U.S. National Stage under 35 USC 371 patent application, claiming priority to Serial No. PCT/NL2020/050421, filed on 26 Jun. 2020; which claims priority from 19187100.3, filed 18 Jul. 2019; the entirety of which are incorporated herein by reference.

The invention relates to a method for recovering a bio-catalytically produced organic substance from a reaction mixture. The invention further relates to a bioreactor system for biocatalytically producing a substance and to the use of the bioreactor system in the biocatalytic production of a substance.

It is known in the art to produce organic substances by fermentation. In such a fermentation process, micro-organisms are used to convert a suitable substrate into an organic substance of interest. As is generally known in the art, various micro-organisms are known that can be used on an industrial scale for the production of a wide variety of organic substances. Generally known fermentative processes include the use of natural micro-organisms, e.g. yeasts or bacteria, for the production of various organic substances, e.g. alcohols, esters, amino acids, carbohydrates, lipids, ketones, aldehydes, organic acids and processes wherein use is made of genetically modified organisms. Organisms may be genetically modified to increase the product titre of a naturally produced organic substance and/or to enable a micro-organism to produce an organic substance that it does not produce naturally. E.g. a micro-organism may be modified by incorporating genes from a plant responsible for the production of a terpene, a terpenoid or other organic substance not naturally produced by the micro-organism.

Another form of biocatalytic production of organic substances makes use of one or more enzymes catalysing the conversion of a substrate into the organic substance of interested, wherein the enzymes are isolated from the natural environment (isolated from the organism it has been produced in), for instance as a solution, an emulsion, a dispersion, (a suspension of) freeze-dried cells, a lysate, or immobilised on a support. The use of an enzyme isolated from the organism it originates from may in particular be useful in view of an increased flexibility in adjusting the reaction conditions such that the reaction equilibrium is shifted to the desired side. Also, the reaction mixture wherein the organic substance is produced may be less complicated: no nutrients for maintaining cells alive are needed and the secretion of irrelevant substances by living organisms is avoided.

Reaction mixtures obtained in biocatalytic processes tend to be rather complex, especially when living micro-organisms or cell-mass of non-living micro-organisms is used. The reaction mixtures comprise typically the biocatalyst, substrate, nutrient (in case living organisms are used), the produced organic substance, and possibly side-products, e.g. fermentation gas which is optionally produced (e.g. $CO_2$) or other substances secreted by the biocatalyst (in case organisms are used).

Various methods have been proposed to recover fermentatively produced organic substances from a fermentation mixture. For hydrophobic organic substances, such as hydrocarbons and lipids, methods can be used that rely on the low water-miscibility of the lipids or hydrocarbon with the aqueous medium. Extractive techniques are also a known possibility.

E.g., EP 2 196 539 describes the use of different solid-liquid-liquid separation techniques to separate the lipid and hydrocarbon biofuels from a fermentation mixture, which lipid and hydrocarbon biofuels have been produced in a column reactor. It is not disclosed to produce the product of interest and separate it from the fermentation mixture in a single apparatus, nor to simultaneously carry out production and separation. Further, it is not disclosed to maintain droplets, bubbles or particles of the product recovery phase dispersed in the reactor within a particular range. Back-extraction for recovering the product is not disclosed either.

WO 2007/139924 is directed to a method for producing and separating bio-organic compounds in a two-phase system, which system comprises an aqueous medium with host cells as a first layer and a liquid organic second phase comprising the bio-organic compound produced by the host cells.

WO 2012/024186 is directed to a purification process wherein a composition comprising a surfactant, host cells and a bio-organic compound is heated, thereby destabilizing the emulsion.

WO 2010/123903, US 2009/029445 and US 2012/129244 describe processes for harvesting the intracellular components from an aqueous solution comprising microorganisms, in particular algae. These processes include rupturing the cell walls of the microorganisms in order to release the intracellular components into the aqueous solution. A disadvantage is that the product is obtained as part of a foam, such that further phase-separation (e.g. decanting, centrifugation) is still required in order to isolate the product.

WO 2015/130167 relates to method for recovering a lipid or hydrocarbon from a fermentation mixture, produced in a fermentation vessel or in a first compartment of a fermentation reactor, which mixture comprises an aqueous phase and a liquid product phase comprising the lipid or hydrocarbon; and feeding at least part of the aqueous phase and part of the liquid product phase to a second vessel or to a second compartment of the fermentation reactor, thereby forming a second mixture; and promoting phase-separation of the aqueous and product phase by injecting a gas into the second mixture, thereby separating the product phase from the aqueous phase.

WO 2017/220957 relates to a method for producing and separating lipid products, wherein a broth comprising a lipid is produced in a fermenter, and wherein the broth comprising the lipid is transferred to a separator, wherein a lipid phase comprising the lipid product is allowed to separate from other constituents of the broth.

Bednarz et al (*J Chem Technol Biotechnol* (2018) studied the reactive extraction of the polyamide monomer hexane-1,6-diamine from cell-containing medium. However, the diamine was not produced using a biocatalyst. According to Bednarz, optimal drop diameter in extraction processes should lie between 1.5 and 2.5 mm.

Lu and Li (Journal of the Taiwan Institute of Chemical Engineers 45 (2014) 2106-2110) propose an integrated in situ extraction-gas stripping process for running batch Acetone-Butanol-Ethanol (ABE) fermentation.

There is a need for alternative methodologies and bioreactor systems for (fast) recovering the produced organic substance of interest from the reaction mixture, e.g. because the known methodology is specific in its application towards the type of produced organic substances (e.g. to lipids or hydrocarbons), towards the type of process (e.g. only batch, only aerobic, only anaerobic or only anoxic), or is limited in terms of maximum micro-organism or produced organic substance concentrations.

Product recovery from the reaction mixture wherein it has been produced (such as a fermentation broth) can be complicated due to the complex composition of the reaction mixture and/or the recovery process can affect the biocatalyst, such as micro-organisms used for the production of a compound of interest, especially when aiming to perform in-situ extraction (such as liquid-liquid (L-L extraction) and separation in a single reactor vessel. This can be accomplished by separation by CIRCOX™ based liquid flow pattern on liquid-liquid broth mixture. The lighter liquid is then given the opportunity to move to a separation section inside the reactor vessel. Liquid-liquid emulsion stability may be destabilized by gas enhanced oil recovery (GEOR).

A poor combination of biomass/cell debris/antifoam/solvent type and concentration can lead to no or no significant organic phase separation, inversely a correct choice of biomass/antifoam/solvent will allow significant organic phase separation.

Further, next to inhibition of catalyst activity by inhibiting (e.g. toxic) concentrations of produced product of interest, side-product and/or the presence of inhibiting compounds in the substrate for the biocatalyst used for the production of the product of interest, in case the biocatalytic conversion is carried out under aerobic conditions, there is a limitation to the oxygen-supply rate for microbial conversion. This does not match the very high oxygen demand strains. For large scale production oxygen demand problems often are compounded.

Furthermore, strains with extractive solvents have been shown to be frequently hampered by emulsion formation of the organic phase. This stable emulsion is then end-of-pipe treated during downstream processing and this is can be a difficult L-L separation (see e.g. Appl Environ Microbiol 2004, October 70(10): 6333-6336, https://www.ncbi.nlm-.nih.gov/pmc/articles/PMC522095.

In particular there is a need for a method or bioreactor system that allows intensified use of a bioreactor system, e.g. in terms of increased overall volumetric production rates (intensified reactor), less product degeneration, less product losses (higher yield), or in terms of reduced floor space (compactness of the reactor system).

In particular the inventors realized that it would be desirable to provide a method or bioreactor system which allows efficient recovery of a biocatalytically produced organic substance, also when the concentration of produced substance in the reaction mixture is kept at a relatively low level in the aqueous phase (such as a fermentation broth). Efficient recovery at low concentrations is a challenge, yet a low concentration in the reaction mixture is generally advantageous in terms of maintaining a relatively high production rate, when the produced substance is potentially toxic or inhibiting to the biocatalyst.

The inventors found that it is possible to overcome one or more problems encountered in the above described prior art respectively to address one or more of the above mentioned needs or desires by carrying out biocatalytic production of the organic substance and separation of a phase comprising the organic substance from the remainder of the reaction mixture wherein the production and separation are carried out simultaneously in a single apparatus comprising a reaction section (such as a fermentation compartment) and a separation section.

Figure 1:
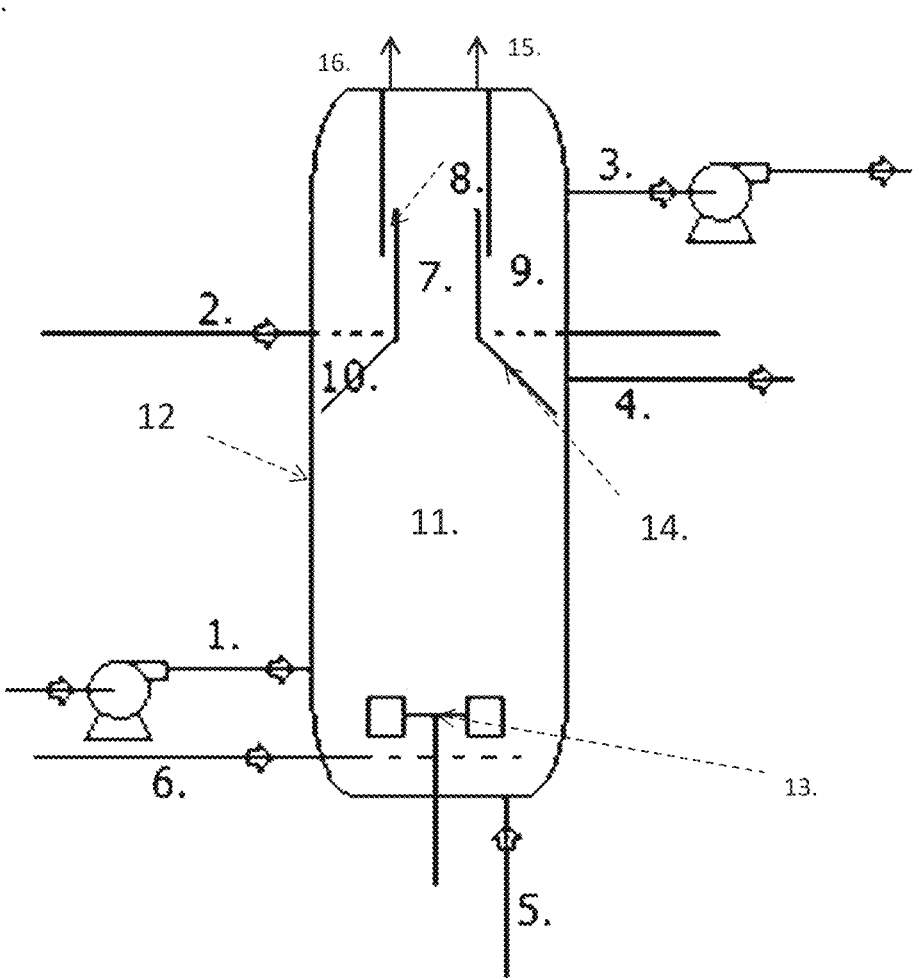
FIG. 1 is a schematic representation of a bioreactor system comprising a reaction compartment and a separation compartment arranged in a single apparatus, including a riser, downcomer, recycle provision, and inlets and outlets for substrate, gas, and product recovery phase.

One or more further objects of the invention which may be addressed follow from the remainder of the description.

Thus, the present invention relates to a method for recovering a biocatalytically produced organic substance from a reaction mixture, comprising providing a reaction mixture, wherein the organic substance is produced using a biocatalyst, which reaction mixture comprises a substrate for the biocatalyst in a continuous aqueous phase, and wherein further a product recovery phase is present (typically dispersed in the continuous aqueous phase) into which the organic substance migrates or onto which the organic substance absorbs or adsorbs; and separating the product recovery phase comprising the produced substance from the aqueous phase and the biocatalyst;

wherein the production of the organic substance and the separation of the product recovery phase are carried out in an apparatus comprising a reaction section containing the reaction mixture wherein the substance is produced and a separation section wherein the product recovery phase comprising the produced substance is separated from the aqueous phase (the aqueous phase comprising dispersed biocatalyst if a dispersed biocatalyst is used), wherein the method comprises a simultaneous production and separation stage wherein at least during said simultaneous stage substrate and/or product recovery phase is fed into the reaction section continuously or intermittently, flow conditions in the reaction section are turbulent flow conditions, reaction mixture—of which mixture the product recovery phase comprises the produced substance—is fed continuously or intermittently from the reaction section into the separation section in which separation section the product recovery phase is separated from the aqueous phase, and product recovery phase, comprising the biocatalytically produced substance, is recovered continuously or intermittently from the separation section of the apparatus.

The reaction section and the separation section generally are separate compartments in the same apparatus, such as separate compartments in a single reactor vessel.

The biocatalyst is generally dispersed (in case of microorganisms or a solid biocatalyst, such as enzymes on a solid carrier) or dissolved (e.g. water-soluble enzymes) in the continuous phase.

Usually a fluid recovery phase is used, typically a liquid, in which case droplets of the recovery phase are dispersed in the continuous aqueous phase, inside the reaction section. Alternatively or in addition a gaseous recovery phase can be used, in which case bubbles of the recovery phase are dispersed in the continuous aqueous phase, inside the reaction section. Alternatively or in addition, a solid recovery phase can be used, in which case particles of the recovery phase are dispersed in the continuous aqueous phase, inside the reaction section. Suitable solid recovery materials can be chosen amongst known adsorbents for an organic substance of interest. Preferably the adsorbent particles, e.g., beads, have a lower density than the aqueous phase, such that they can be recovered by flotation. Such particles are known in the art and include polymeric adsorbent particles, in particular functionalized polymeric particles.

The inventors found in particular that the present invention allows matching of the In Situ Product Recovery power (i.e. ISPR-power, a measure for the level of migration of produced organic substance into the product recovery phase) and the separation capacity, (i.e. SC). This is typically achieved by maintaining the migration/adsorption/absorption rate of the produced substance into/onto the product recovery phase in the reaction section at about the same rate as the rate at which produced substance (as part of the separated product recovery phase) is separated from the aqueous phase in the separation section and/or by maintaining the migration/adsorption/absorption rate—which rate may also be referred to herein as the extraction rate—'of the produced substance into/onto the product recovery phase in the reaction section at about the same rate as the rate at which the substance is produced.

Generally, this is accomplished by having relatively small particles, bubbles or droplets of the product recovery phase dispersed in the reaction mixture inside the reaction section. If droplets, particles or bubbles of the product recovery phase become too large, extraction rate becomes too low to maintain extraction rate and production rate at least substantially at the same rate. Thus, usually the (spherical) droplets, bubbles or particles have an average (arithmetic) diameter of about 10 micrometer to 150 micrometer, although in practice one may allow a higher diameter, in particular of up to 250 micrometer, whilst maintaining said production rate and said migration/adsorption/absorption rate at about the same rate. As used herein the particle/droplet/bubble size of the product recovery phase in the reaction compartment is the Sauter mean diameter (D[3,2]). Sauter mean diameter, which is the ratio of the cube of the volume mean diameter to the square of the surface mean diameter; roughly the ratio of the particle volume to its surface area" (aiche.org), is commonly used in the art not only to express sizes of spherical particles but also of non-spherical shapes/deformations. Sauter mean diameter, D[3,2], as used herein is as measured by an optical method by particle data analysis on volume, area and diameter, in particular to Maaß, Sebastian & Rojahn, Jürgen & Hänsch, Ronny & Kraume, Matthias. (2012). *Automated drop detection using image analysis for online particle size monitoring in multiphase systems. Computers & Chemical Engineering.* 45. 27-37. 10.1016/j.compchemeng.2012.05.014 (https://www.researchgate.net/publication/256937907_Automated_drop_detection_using_image_andalysis_for_online_particle_size_monitoring_in_multiphase_systems) with reference to https://SOPAT.de SOPAT.de (as described in the present Examples). In practice, D[3,2] can also be estimated by calculation.

Sauter mean diameter (D[3,2]) of the droplets, bubbles respectively particles of the dispersed product recovery phase in the reaction section is generally within the range of about 10 to about 150 μm, although a method according to the invention may be operated at a higher D[3,2], in particular at an D[3,2] in the range of 150-250 μm. The inventors found that a D[3,2] within the range of about 10 to about 150 μm a method of the invention is both sufficiently effective from product recovery phase buoyance perspective and from a product extraction perspective (mass transfer area availability vs droplet diameter). As a rule of thumb, the lower D[3,2] the higher the rate at which the product leaves the aqueous phase into/onto the product recovery phase, yet the more difficult/slower separation of the product recovery phase comprising the organic substance of interest will be. Thus, the inventors realized maintaining D[3,2] within this range is a very useful measure to match ISPR and SC. Preferably, D[3,2] is within the range of about 15-100 μm, in particular within the range of about 20-90 μm, more in particular 40-80 μm. A D[3,2] of more than 150 μm, in particular of up to about 250 μm can still give satisfactory results. Such D[3,2] may be the consequence of coalescence of particles/droplets/bubbles that initially had a smaller diameter; an advantage of a relatively large D[3,2] is that it can facilitate separation. Further, the continuous or intermitted addition and removal of product recovery phase provides an extra degree of operational freedom, which can be used to control the effective dispersion characteristics of the product recovery phase (droplet size in case of a liquid, residence time, mass fraction of product recovery phase). As the skilled person will understand, this addition can be done in a controlled manner. This enables work points that reduce or even completely avoids emulsification of the dispersed product recovery phase and the aqueous phase Other means to match ISPR power and SC include the choice of recovery phase, biocatalytic reaction conditions and the driving force for recirculating fluid from the separation section to the reaction section. Various means will be described in further detail below.

During the simultaneous product and separation phase reaction mixture is fed continuously or intermittently into the separation section and product recovery phase is removed continuously or intermittently from the separation section of the apparatus. Further, optionally, gas is introduced into the contents of the separation section. The feeding into, removal from and optional gas introduction into the separation section is generally carried out whilst maintaining at least substantially non-turbulent conditions. When there is a flow in the separation section the flow conditions are generally essentially laminar. It is not necessary that there is a continuous flow though. Essentially laminar flow conditions and no-flow conditions can be alternated. Accordingly, the reaction mixture fed into separation section generally enters said separation section under essentially laminar flow conditions.

I.e. in general when there is motion in the fluids in the separation section, at least during the simultaneous production and separation phase, it is an essentially laminar flow. It is not necessary to maintain a flow into and/or from the separation section throughout the simultaneous stage. Feeding reaction mixture, withdrawal of product, but also the optional introduction of gas and/or optional recycle of aqueous phase can be intermittent. In the absence thereof, separation proceeds. The laminar flow conditions have been found to have a positive effect on separation capacity, in particular when using a difference in density between recovery phase and aqueous phase. The Reynolds number (Re), is a generally known dimensionless number defined as the ratio of inertial forces to viscous force (Re=density×fluid velocity×characteristic length/dynamic viscosity), that is used in the art to quantify the flow conditions. A low Re, typically of about 2300 or less is indicative of laminar flow, preferably of 2000 or less, e.g. 100-1800. A high Re, typically of about 2900 or more, e.g. 3500-10000, is indicative of turbulent flow. However, a person skilled in chemical engineering will also be able to determine visually whether flow conditions are essentially laminar (e.g. by injecting some ink and watching the flow pattern).

A major advantage of the present invention is that the ISPR power and the separation capacity are matched in a single apparatus (integrated approach).

A further major advantage is that the present invention allows preventing the production rate to slow down by keeping the concentration of the produced organic substance in the reaction section low, whilst remaining effective recovering the organic substance from the reaction mixture. It has been found possible to increase daily production capacity, at least for a number of hydrophobic products, more than 10 fold, even up to close to 100 fold for specific products.

A further major advantage is that the simultaneous operation allows at least substantially continuous processing, wherein a high production capacity is achieved whilst reaction mixture is at least substantially continuously removed from the reaction section. Applying essentially continuous or intermittent removal of reaction mixture (including product recovery phase) from the reaction section allows for keeping the concentration of the organic substance of interest that is produced and/or the concentration of other potentially reaction-inhibiting substances low, i.e. below level substantially inhibiting the catalytic activity. This also allows the use of substrate/nutrient originating from crude materials, comprising potentially inhibiting substances, such as one or more phenols.

The invention further offers an advantage because it provide a way to increase the volumetric productivity. This is useful, especially, when a non-growing or slow growing biocatalyst is used, e.g. when the biocatalyst comprises an enzyme. A high volumetric rate is in particular achieved by the recycle of the biocatalyst. In this case the biocatalyst remains suspended and the inhibiting product or by-product is being removed, while the reaction remains ongoing in the reaction compartment.

The invention further relates to a specific bioreactor system, namely a bioreactor system for biocatalytically producing a substance, comprising an apparatus, said apparatus comprising a reaction compartment (11) situated in a lower part of the apparatus and a separator compartment (9), a riser (7) defining a channel at or near the top of the reaction compartment (11) adapted to allow fluid from the reaction compartment to flow upward, a downcomer (8) defining a channel between the outlet side of the riser (7) and the inlet side of the separator compartment (9), adapted to allow (non-gaseous) fluid leaving the riser (7) to flow downward into the separator compartment, the reaction compartment (11) comprising an agitator, preferably a stirrer, a feed inlet (1) for a substrate for use in the production of the substance,
an inlet (5) for a product recovery phase,
an inlet (5) for a gas phase, preferably a sparger, the separator compartment (9) comprising an outlet for product recovery phase, typically positioned closer to the top of the separator compartment (2) than the outlet end of the downcomer (9), a recycle provision (10) for recycling biocatalyst (typically fluid containing biocatalyst) taken from a part of the separator compartment (9) below the inlet (2) for the gas phase to the reaction compartment (11), and the apparatus having a headspace provided with an outlet for gas phase introduced into the apparatus via the inlets for gas phase (2, 6).

The inlet (5) for a product recovery phase is preferably positioned in the middle part or the bottom part of the reaction compartment, in order to avoid the risk of short cut (product recovery phase leaving the reaction section without having been in thorough contact with the bulk of the reaction compartment, extraction efficiency is substantially decreased). More preferably, inlet (5) is positioned closer to the bottom of the reaction compartment than the feed inlet (1) for substrate. This is preferred because then the distribution in the reaction compartment is better (better mixed). Further, inlet (6) for the gas phase, is typically positioned closer to the bottom of the reaction compartment than the feed inlet (1) for substrate and also closer to the bottom of the reaction compartment than the inlet (5) for the product recovery phase.

The invention further relates to the use of a bioreactor system according to the invention in the biocatalytic production of an organic substance. The bioreactor system can in particular be used for a method according to the invention.

For the purpose of clarity and a concise description features are described herein as part of the same or separate embodiments, however, it will be appreciated that the scope of the invention may include embodiments having combinations of all or some of the features described.

The term "or" as used herein is defined as "and/or" unless specified otherwise.

The term "a" or "an" as used herein is defined as "at least one" unless specified otherwise.

When referring to a noun (e.g. a compound, an additive, etc.) in the singular, the plural is meant to be included.

The term "(at least) substantial(ly)" or "essentially" is generally used herein to indicate that it has the general character or function of that which is specified. When referring to a quantifiable feature, this term is in particular used to indicate that it is at least 50%, more in particular more than 75%, even more in particular more than 90% of the maximum that feature. The term 'essentially free' is generally used herein to indicate that a substance is not present (below the detection limit achievable with analytical technology as available on the effective filing date) or present in such a low amount that it does not significantly affect the property of the product that is essentially free of said substance. In practice, in quantitative terms, a product is usually considered essentially free of a substance, if the content of the substance is 0-1 wt. %, in particular 0-0.5 wt. %, more in particular 0-0.1 wt. %.

In the context of this application, the term "about" means generally a deviation of 10% or less from the given value, in particular a deviation of 5% or less, more in particular a deviation of 2% or less.

The term "fluid" is used herein for liquids and mixtures of liquids and at least one other phase, such as suspensions, dispersion, that flow without applying external pressure (pressure other than gravity).

As used herein "organic substance' includes any organic substance that is chemically oxidisable, as can be determined by the Chemical Oxygen Demand (COD) test, as described in ISO 6060:1989.

The skilled person is familiar with terms like 'upper', 'lower', 'middle', 'at bottom', 'near bottom', 'at top' and 'near top'. Generally these are read in relation to another, and the skilled person will be able to reduce implementation thereof to practice, based on common general knowledge, the information and citation disclosed herein, and the specifics of a unit (such as bioreactor, a separate container, or a volume of matter contained in the bioreactor or a section) of the installation.

As a rule of thumb, unless follows differently from the context, 'near' a certain reference point (such as 'bottom' or 'top') usually means 'at a relative height of up to +/−20%' from the reference point', in particular s 'at a relative height of up to +/−15%' from the reference point' more in particular 'at a relative height of up to +/−10%' from the reference point. The relative height is the distance from the bottom divided between the total height of the unit (height difference between bottom and top).

As a rule of thumb, unless follows differently from the context, an 'upper' (top) part generally means in the upper ½, and in particular in the upper ⅓ of the unit, a 'lower' (bottom) part generally means the lower ½ of the unit and in particular the lower ⅓ of the unit. When referring to a middle part, this in particular means the middle ⅓ of the unit (from ⅓ of the bottom to ⅓ from the top).

The term 'biocatalytical(ly)' is generally known in the art to describe methods wherein at least one reaction step in the method is catalysed by a biological material or moiety derived from a biological source, for instance an organism or a biomolecule derived there from. The biocatalyst may in particular comprise one or more enzymes. The biocatalyst may be used in any form. In an embodiment, one or more enzymes are used isolated from the natural environment (isolated from the organism it has been produced in), for instance as a solution, an emulsion, a dispersion, (a suspension of) freeze-dried cells, as a lysate, or immobilised on a support. In an embodiment, one or more enzymes form part of a living organism (such as living whole cells). Particularly good results have been achieved with living cells, in particular with yeast cells and with bacterial cells. Processes wherein the biocatalyst comprises a living cells are also referred to in the art as 'fermentative' methods. The present invention can be used for anaerobic processes, aerobic processes and anoxic processes. Although there are various examples in the prior art of anaerobic processes, it is often desired in the art to be able to work under aerobic conditions if a high production rate is desired, since anaerobic processes often have a relatively low production rate due to a lower availability of reaction energy, as oxygen is a very good way to generate ATP. Aerobic fermentations tend to run at oxygen transfer rate limiting conditions and the production rate cannot be readily improved further. The present invention offers a surprising advantage that a higher than usual production rate can be maintained for anaerobic processes. This has amongst others been found possible due to the fact that no oxygen transfer limitation can occur, which is a current known bottleneck in aerobic industrial fermentation processes. Also less heat is generated in anaerobic fermentations (than in aerobic processes), whereby a further intensification is possible and cooling of the system does not pose an engineering limitation on the system. Anaerobic reaction systems that are at risk of facing inhibition/toxicity by too high a concentration of produced organic substance (or other component(s), additionally benefit from the intensified method of the invention since the risk of such inhibition/toxicity is avoidable by using extraction with the product recovery phase, in particular liquid-liquid extraction during fermentation as the oxygen transfer limitations in (bulk scale) aerobic fermentations systems do not apply for anaerobic systems.

The method according to the invention can be commenced with a batch stage, wherein the reaction section is provided with an aqueous phase comprising the substrate and the biocatalyst, preferably dispersed or dissolved in the aqueous phase. The biocatalytic conversion of substrate to the organic substance of interest can start in the batch stage. During the batch stage, gas (such as oxygen containing gas) may be added. The recovery phase may also be introduced in the batch stage or be added subsequently. One can choose when to proceed from the batch stage to the simultaneous production and separation stage. E.g. the batch stage can be continued till a predetermined part of the substrate has been consumed, or until essentially all substrate has been consumed. The batch stage can be continued till a target concentration for the produced organic substance in the reaction section is reached. One may also proceed to the simultaneous production and separation stage based on reaching a predetermined biocatalyst activity towards production of the organic substance (such as proceed at a point where the catalytic reaction is no longer essentially non-inhibited. The biocatalyst activity towards production of the organic substance is usually essentially non-inhibited by the presence of the organic substance, at least during the simultaneous stage, and/or the concentration of biocatalyst-inhibiting contaminants originating from the substrate is maintained at a value at which the biocatalyst activity towards production of the organic substance is essentially non-inhibited by the presence of the contaminant, at least during the simultaneous stage, and/or the concentration of side-product is maintained at a value at which the biocatalytic activity towards production of the organic substance is essentially non-inhibited by the side-product, at least during the simultaneous stage. Preferred concentrations for the organic substance in the reaction section (and of other components) is dependent on the type of substance (component). Usually the concentration of at least the organic substance of interest, and more preferably of other components is kept at a value at which they are essentially non-toxic to the biocatalyst, or at least wherein the concentration is not a limiting factor in the total production capacity of the apparatus wherein the method is carried out, at least during the simultaneous stage. Advantageously, the concentration of the organic substance during the simultaneous stage is such that the total production rate activity is 50-100%, preferably 80-100%, more preferably 90-100% or more preferably 95-100% of the maximum activity under otherwise the same non-inhibiting conditions.

The method according to the invention allows to operate the reaction section under continuous stirred tank reactor (CSTR) conditions, with an essentially steady state, at least in terms of the organic substance concentration. In such case preferably an agitation means in a bottom part of the reaction section is used, more preferably a bottom stirrer. Other types of reactor types can be used, e.g. a gas lift type reactor or a bubble column. It is also possible to combine reactor principles, such as a CSTR or CSTR-like (e.g. pulse-fed) reactor in combination with air lift. Steady state conditions are not generally reached in known fermentation processes. It is advantageous to keep the concentration of the produced substance in the reaction section essentially constant during the simultaneous stage. Herewith the high production rates are maintained. Optimal concentrations depend on factors such as the organic substance of interest, the biocatalyst and the recovery phase. If desired, a provision is present in the reaction section to monitor, the concentration of the organic substance. Further, a provision may be present to regulate the concentration, such as a controller adapted to change a parameter relevant to the concentration when the concentration deviated too much from a set-point or set-range concentration. Relevant parameters include feed rate of the substrate, addition rate of recovery phase, withdrawal rate of reaction mixture from the reaction section, concentration of biocatalyst and temperature.

Irrespective of equipment to regulate the concentration of organic substance in a section of the apparatus, the present invention has some innate self-correcting properties, especially when producing an organic substance that is potentially inhibiting/toxic to the biocatalyst and/or when one or more other components are present in a section of the apparatus that can be toxic/inhibiting to the biocatalyst or can have an effect on separation efficiency. E.g. if the product recovery rate becomes higher than the production rate, this leads to lower present product concentrations in the aqueous phase in the reaction section, leading then to higher productivities (as e.g. inhibiting conditions are now less) and high overall product recovery. The control of the organic phase recovery and (continuous) flow behaviour enables opportunities with solvent dosing strategies and conditions. It enables the control of the organic phase recovery and the flow behaviour. E.g. a low solvent concentration in the reaction section can actively be achieved and maintained, while still having enough extraction product, but no net accumulation of solvent in the fermentation compartment.

As will be discussed in further detail below, measures like the choice of the recovery phase, average flow rate for feed into the reaction section, withdrawal rate of reaction mixture from the reaction section and rate at which reaction mixture is fed into the separation section, recycle of aqueous phase from the separation section to the reaction section, withdrawal rate of product recovery phase comprising the organic substance from the apparatus, withdrawal of aqueous phase (which may contain dispersed biocatalyst) from the apparatus and the optional addition of chemicals (surface active chemical, extractant, co-solvent) at e.g. either top of at controlled point in the separation compartment, can be used to maintain the concentration of the organic substance in the reaction section at a desired level.

During the simultaneous stage, feed into the reaction section, withdrawal of reaction mixture from the reaction section, feed into the separation section and withdrawal rate of product recovery phase comprising the organic substance from the separation section is done continuously or intermittently. For a steady state operation, mass balance is maintained, i.e. the volume fed into the apparatus (such as feed of aqueous phase comprising substrate and optionally nutrients and feed of recovery phase) is kept at essentially the same rate as the volume removed from the apparatus (such as product recovery phase comprising the organic substance withdrawn from the separation section). The continuous feed does not have to be at a constant rate. It is also possible to feed a volume intermittently (pulse-feed), in which case withdrawal of an about the same volume from the apparatus is typically also done intermittently. When feeding/withdrawing intermittently, the interval between feeding/withdrawing periods and periods without feeding/withdrawing as well as the duration of such periods can be chosen within wide ranges, based on common general knowledge and the information disclosed herein plus option-
ally a limited amount of trial and error. As a rule of thumb,
when withdrawing/feeding intermittently this is usually
done at least once a day. Practically, as the number of times
per day increases, the feeding/withdrawal will approach
essentially continuous conditions. E.g. an intermittent feed/
withdrawal can be done as often as 300 time a day (about
once every 5 min) or even more often. In particular, when a
feed or withdrawal is done intermittently, this is advanta-
geously done 2 to 100 times a day, more in particular 4-48
times a day, e.g. 6-24 times a day, for practical reasons
usually with about equal interval.

For maintaining the concentration of the organic sub-
stance in the reaction section at an advantageous level, it is
further preferred, at least during the simultaneous produc-
tion and separation stage the substrate and the product
recovery phase are fed into the reaction section at a rate at
which the production rate of the substance and the migration
rate of the produced substance into the product recovery
phase respectively the adherence rate to the product recov-
ery phase are about the same. If the production rate and the
rate of migration into/adherence onto the recovery phase are
not about the same, conditions in the reaction section can be
changed e.g. as follows:

Reduction of D[3,2] will increase migration into/adher-
ence onto the recovery phase. This can be accom-
plished by increasing the degree of turbulence (more
agitation, e.g. increasing the rotation speed in case a
stirrer is used) Likewise increase of D[3,2] will
decrease migration into/adherence onto the recovery
phase.

Feed rate of product recovery phase into the reaction
section can be increased to increase migration into/
adherence onto the recovery phase. Likewise reduction
of feed rate will have the opposite effect.

Increase of feed rate of substrate and/or increase of
biocatalyst concentration can be used to increase pro-
duction rate, and thereby concentration of organic
substance. Likewise, a reduction will have an opposite
effect.

Temperature can be changed. Effects depend on type of
biocatalyst, partitioning coefficient and product recov-
ery phase and existent temperature.

It is an advantage of the present invention that the overall
ratio product recovery phase to water in the reaction mixture
can be relatively high, in particular compared to a 'normal'
extractive batch process (that e.g. operates at effective
solvent amount 10 (% v/v), even up to 30-50 times higher,
at a similar daily production capacity. Besides the mainte-
nance of the product concentration or other potentially
inhibiting components at a substantially non-inhibiting level
for the biocatalyst, a reason for this improvement resides in
the fact that not the whole volume of product recovery phase
is present all at once in the reaction section as compared to
a conventional batch process. A conventional batch process
adds once product recovery phase and harvests all together
at the end of the batch phase.

Usually, the weight to weight ratio product recovery phase
to aqueous phase in the reaction mixture is in the range of
0.005-0.30 preferably 0.01-0.20, in particular 0.02-0.1. A
high ratio allows effective migration into/adherence onto the
product recovery phase, also at a relatively low organic
substance concentration in the reaction mixture. With choice
of the recovery phase, addition rate and feed rate of sub-
strate, a net aqueous phase dilution rate is applied to the
system and this allows operation at a high retention of biocatalyst. This leads to higher biocatalyst concentrations
and higher overall volumetric productivities.

For the product recovery phase typically a compound or
mixture of compounds is used that is at least substantially
insoluble in water. Typically the aqueous solubility is less
than 85 g/l, in particular less than 10 g/l, preferably 0-1 g/l,
at least at the temperature(s) at which it is contacted with the
fermentation medium and/or at ambient temperature (25°
C.). Further, the product recovery phase is usually chosen
based on the organic substance that is to be recovered, i.e. it
is a phase for which the produced substance has a higher
affinity than for the aqueous phase in which the product
recovery phase is dispersed. Thus, the organic substance of
interest is removed from the aqueous phase by phase affinity
difference. Suitable phases can be selected for an organic
substance of interest based on common general knowledge
or empirically. Preferably, the product recovery phase is a
phase for which the produced substance has a partitioning
coefficient (i.e. the ratio of the equilibrium concentration of
the produced substance in the product recovery phase to the
equilibrium concentration of the produced substance in the
aqueous phase) under the conditions existing in the reaction
section of at least 3, preferably of 5-1000, more preferably
of 7-250, in particular 10-100. The higher the partitioning
coefficient, the higher the migration/adherence rate into/onto
the product recovery phase. On the other hand, if subsequent
separation of the organic substance from the recovery phase
is desired, this may become more complicated if the parti-
tion coefficient is extremely high, at least for some organic
substances.

A further property to consider when choosing the product
recovery phase is the density of the product recovery phase.
A difference in density with the aqueous phase is desirable
because this allows separation by gravitation or centrifug-
ing. Particularly good results have been achieved with a
recovery phase having a lower density than the aqueous
phase.

Inside the reaction section, the product recovery phase is
dispersed in the continuous phase. However, the product
recovery phase does not need to be emulsified. Typically, the
method according to the invention is carried out advanta-
geously without added emulsifiers or other added disper-
sion-stabilisers, also in case of a liquid recovery phase. In
accordance with the invention the product recovery phase is
usually kept dispersed due to maintaining the turbulent
conditions (agitating sufficiently forcefully). A major advan-
tage of working without added emulsifiers (or other added
dispersion-stabilisers) is that the absence thereof facilitates
separation of the recovery phase from the aqueous phase in
the separation section. Further, when not used, there is no
need to remove them afterwards.

Preferably, a liquid recovery phase is used for product
recovery. A liquid recovery phase is very useful for extrac-
tion of a produced organic substance. Typically a liquid
phase is used that forms a separate layer from the remainder
of the reaction mixture (aqueous phase, typically also com-
prising biocatalyst if a dispersed or dissolved biocatalyst is
used) in the separation section. Such separation technique is
generally known in the art of separation technology as a
gravity settling technique. In accordance with the invention
it is not necessary that the recovery phase is completely
removed from the remainder of the reaction mixture. It is
sufficient that a layer of recovery phase that is at least
enriched in recovery phase, containing the organic substance
is formed. A method according to the invention allows
recovery of 80-100% of the recovery phase, preferably 90%
or more of the recovery phase, more preferably 95% or more of the recovery phase, from the reaction mixture. The recovery-phase layer (product layer) is generally at least substantially free of aqueous phase. At least during the simultaneous stage reaction mixture, containing recovery phase, will be fed into the separation section, typically below the interface between the recovery phase layer if the recovery phase is less dense respectively above the interface if the recovery phase is more dense than the remainder of the reaction mixture. Generally, more remote from the interface between the layers the fraction of recovery phase in the remainder of the reaction mixture will be less and at least in some embodiment, a zone is present in the separation section that is essentially free of recovery phase.

In an apparatus according to the invention, when used in a method according to the invention, the layer is formed on top of the remainder of the reaction mixture.

Particularly suitable liquids for the product recovery phase are organic liquids, in particular hydrophobic organic liquids, which form a phase separate from the aqueous phase of the reaction mixture. Preferred liquids are alkanes, in particular alkanes having 6 carbons (C6) or more, preferably C7-C25, e.g. C7-C15. Specific examples of particularly suitable liquid alkanes are hexanes, heptanes, octanes, nonanes, decanes, dodecanes and pentacosane). The alkane may be linear or branched or cyclic. Good results have, amongst others been achieved with dodecane. Further, liquid hydrophobic alcohols are particularly suitable. Preferably the alcohol is selected from C8 alcohols and higher, more preferably C10-C20 alcohols. The alcohol may be linear or branched or cyclic. Specific examples of particularly suitable alcohols are an octanol, a decanol, a dodecanol, oleyl alcohol. Further, liquid triglycerides are particularly suitable, preferably vegetable oils. Particularly preferred examples are castor oil, sunflower oil and soy(bean) oil. The various examples of liquids for the recovery phase that are given are not or poorly soluble in water. Furthermore they typically show good biocompatibility, which is of interest when using a living cell for the biocatalysis.

In addition or alternatively a gas phase can be used as product recovery phase. This can in particular be interested in case the organic substance of interest is volatile, e.g. a volatile flavour or fragrance component. The gas can be produced in situ (fermentation gas, especially in case of anaerobic/anoxic conditions but also in aerobic systems) or can be introduced into the reaction section via an external feed, e.g. air or oxygen (in case of aerobic conditions), carbon dioxide, or nitrogen or another inert gas.

In addition or alternatively a solid phase can be used as product recovery phase. Examples thereof are known adsorbents for organic substances, e.g. Zeolite materials (ZSM-5), amberlite resins, coated resins/zeolites.

Apart from being useful as product recovery phase, gas can also advantageously be introduced into the reaction section to create a gas lift effect. This is in particular useful in an embodiment wherein the reaction mixture leaves the reaction section at or near the top of the reaction section. This is usually the case when a fluid recovery phase is used having a lower density than the aqueous phase. The gas lift then allows flow of the reaction mixture from the reaction section to the separation section without needing a mechanical pump. In case of an aerobic process, the gas (oxygen/air) also can be used to provide oxygen to the micro-organisms catalyzing the production of the organic substance. Thus, in a preferred method of the invention at least during the simultaneous stage a gas is fed in a lower part of the reaction section which gas generates or contributes to an upwards motion of the reaction mixture, whereby reaction mixture flows into a riser situated between the reaction section and the separation section providing a transport channel between said sections and from the riser into the separation section.

As the mixture flows further downstream from reaction section to the separation section, flow conditions will become less turbulent (Re is reduced) and the flow regime will eventually become essentially laminar, at least in the separation section (9) where recovery phase is separated from the aqueous phase. Generally, at least when using a liquid recovery phase with lower density than the aqueous phase, during the simultaneous stage, reaction mixture flows from a riser into a downcomer; then the flow regime generally changes from a turbulent to an essentially laminar one in the downcomer. Thus, the risk of some unacceptable turbulent behaviour in the separation section (9) is avoidable. Moreover, the reduced turbulence and transition to essentially flow laminar conditions in the downcomer facilitates gas bubbles in the downcomer to move upward, and escape the reaction mixture in the downcomer. Thus, advantageously, in the downcomer gas still dispersed in the reaction mixture is allowed to separate from the liquid reaction mixture. From the downcomer the reaction mixture flows further downstream into the separation section, wherein the product recovery phase comprising the produced organic substance is separated from the remainder of the reaction mixture.

This is typically accomplished by allowing the reaction mixture to settle into a layer enriched in product recovery phase, including produced organic substance (i.e. the product layer) and a layer with a reduced content of product recovery phase, compared to the reaction mixture entering the separation section (i.e. the remainder of the reaction mixture). Preferably, the layer enriched in product recovery phase at least substantially consists of product recovery phase, including the produced organic substance. The remainder of the reaction mixture is typically an aqueous phase, containing at least a substantially part of the biocatalyst. Preferably essentially all of the biocatalyst remains in the remainder of the reaction mixture. If desired, settling into the product layer and the layer of the remainder of reaction mixture can be facilitated by adjusting process conditions, like temperature, or by adding one or more additives selected from the group of surface active chemical, extractants and co-solvent. These are preferably added at or near the top or at controlled point in the separation compartment. Addition at or near the top is e.g. found to result in more effective coalescence of product recovery phase droplets or, where applicable to destabilize emulsions/suppress emulsion formation.

Particularly good results have been achieved with an apparatus wherein the riser (vertically with inlet side at the lower end and outlet at upper end) is positioned centrally in an upper part of the apparatus (along a central vertical axis), the downcomer at least substantially surrounds the riser and at least the part of the separation section wherein a layer of recovery phase at least substantially surrounds the downcomer.

Particularly good results have been achieved with a method wherein a riser and downcomer are used, wherein the product recovery phase is a liquid phase having a lower density than the aqueous phase, wherein downstream of the riser (in the down corner) the reaction mixture comprising the product recovery phase, enriched with produced organic substance, is separated from the gas that generated or contributed to the upwards motion, wherein said reaction mixture separated from said gas is separated in the separation section into an upper layer comprising the product recovery phase enriched with product substance and a lower layer comprising the aqueous phase (typically including biocatalyst if the biocatalyst is a dispersed biocatalyst), wherein product recovery phase enriched with produced substance is recovered from said upper layer, and wherein aqueous phase (typically including biocatalyst if the biocatalyst is a dispersed biocatalyst), from said lower layer is returned to the reaction section.

In case the product recovery phase has a lower density than the aqueous phase, and in particular if the product recovery phase is a liquid phase, the reaction mixture is usually separated in the separation section into an upper layer comprising the product recovery phase enriched with produced substance and a lower layer comprising the aqueous phase (including if present, biocatalyst dispersed or dissolved in the aqueous phase)

wherein product recovery phase enriched with produced substance is recovered from said upper layer.

Preferably at least part of the aqueous phase (including, if present, biocatalyst dispersed or dissolved in the aqueous phase) from said lower layer is returned to the reaction section.

Good results have been achieved with feeding gas into the separation section. However, optionally a gas is fed, e.g. sparged, into the reaction mixture in the separation section at a position below the interface between the upper and the lower layer. This gas is used to promote coalescence of the dispersed product recovery phase and/or to promote upward motion of the product recovery phase. More detailed teaching about this measure can be found in WO 2015/130167, with the proviso that in the present method sparging is done under conditions wherein generally essentially laminar conditions are maintained. Gas can be used as driving force for the liquid circulation within the apparatus and as product removal, e.g. for gas stripping (ISPR already naturally occurring in the system), as well as mixing force in the fermentation compartment. So the gas injection fulfils several functions that is optimized to a continuous (or batch or fed-batch) extractive fermentation. Further, gas injection can be used to create a gas holdup that creates a density difference in the different compartments.

In a preferred embodiment, the separation section comprises a temperature regulation, isolated from the reaction section, which preferably comprises a separate temperature regulation. This allows operation of the reaction section and the separation section at different temperatures, despite the sections being present in the same apparatus and both reaction and separation being carried out at the same time. For separation of recovery phase from aqueous phase, in particular by layer formation, a relatively low temperature is usually preferred (layer formation takes place faster and/or a more effective separation can take place), whereas bio-reactions usually proceed faster at a relatively high temperature (at least up to about 40° C. for most living organisms/enzymes originating from most living organisms, and higher for thermophiles or biocatalysts originating from thermophiles). Nonetheless, in specific embodiments it separation may be improved by at least initially operating the separation section at a higher temperature than the fermentation section. This can, e.g., be useful if the dispersion of the recovery phase is a relatively stable one, e.g. due to the presence of stabilizing components. These are usually not added (purposely), but may be present in the substrate, in particular if a relatively crude material is used, such as a substrate comprising second-generation bio-based feed-stock. Further, stabilizing components may be formed as side-products in the fermentation section, in particular when a living cell is used as a biocatalyst. Increasing the temperature in the separation section, at least temporarily, can then be an effective manner to destabilize the dispersion, whereby coalescence of the dispersed droplets/particles/bubbles is promoted and separation from the aqueous phase is facilitated.

Thus, being able to operate reaction section and separation section at different temperatures in a single apparatus is another measure to match ISPR power and SC. In an advantageous embodiment, the temperature difference between the temperature in the separation section, in particular in a central part of the separation section the temperature in the reaction section in particular a central part of the reaction section, is 2-20° C. In a particularly preferred embodiment said difference is 4-15° C., more in particular 5-10° C. A temperature difference can be maintained essentially throughout the simultaneous phase, or one can alternate the temperature difference between a larger difference and a smaller difference (or no difference) or one can alternate between the temperature in the fermentation section being higher and the temperature in the separation section being higher. Particularly good results have been achieved with a method wherein the temperature in the separation section is lower than in the fermentation section for at least a substantial part of the duration of the simultaneous production (in particular fermentation) and separation stage.

A method according to the invention is in principle suitable for any kind of biocatalyst, including living cells, an isolated enzyme or combination of isolated enzymes and an isolated enzyme or combination of isolated enzymes immobilized on one or more support materials dispersed in the aqueous phase. Particularly good results have been achieved with living cells. More in particular the invention is advantageous in that is allows the use of living cells, that secrete the organic substance into the aqueous phase without having to be lysed. The cell can be naturally capable of doing this, or be genetically modified to improve secretion. The skilled person (e.g. a synthetic biologist) will be able to provide such modification, based on knowledge about the transporters in a cell's membrane.

The possibility to make use of living cells that are not lysed to recover the organic substance facilitates carrying out the method of the invention under essentially continuous production and recovery of the organic substance. In a method wherein the cells are lysed, a large amount of other components are typically introduced into the continuous phase or even the recovery phase, such as intracellular emulsifying/dispersion stabilising substances. Nonetheless, as described herein, there are measures provided to avoid the formation of stable emulsions/dispersions, e.g. by adjusting residence time, degree of turbulence in the reaction section or changing the temperature in the reaction section or the separation section.

The biocatalyst can be or originate from eukaryotic organisms (e.g. mammalian cells, plant cells, algae, fungi) or prokaryotic organisms (bacteria and archaea). Usually, the biocatalyst is or originates from a micro-organism; in particular if the biocatalyst is a living cell or a lysate, a micro-organism is preferred.

Preferably the biocatalyst comprises a micro-organism selected from the group of bacteria, archaea and fungi, preferably selected from the genera *Pseudomonas, Gluconobacter, Rhodobacter, Clostridium, Escherichia, Paracoccus,*

*Methanococcus, Methanobacterium, Methanocaldococcus, Methanosarcina, Aspergillus, Penicillium, Saccharomyces, Kluyveromyces, Pichia, Candida, Hansenula, Bacillus, Corynebacterium, Blakeslea, Phaffia (Xanthophyllomyces), Yarrowia, Schizosaccharomyces, Zygosaccharomyces, Saccharopolyspora* and *Zymomonas* more preferably from the group of *Corynebacterium glutamicum, Escherichia coli, Bacillus subtilis, Bacillus methanolicus, Pseudomonas aeruginosa, Pseudomonas putida Rhodobacter capsulatus, Rhodobacter sphaeroides, Paracoccus carotinifaciens, Paracoccus zeaxanthinifaciens, Saccharomyces cerevisiae, Saccharomyces pastorianus, Schizosaccharomyces pombe, Aspergillus nidulans, Aspergillus niger, Aspergillus oryzae, Blakeslea trispora, Penicillium chrysogenum, Phaffia rhodozyma (Xanthophyllomyces dendrorhous), Pichia pastoris, Yarrowia lipolytica, Saccharopolyspora spinosa* and *Zymomonas mobilis* in particular from the group of *Escherichia coli, Pseudomonas aeruginosa, Pseudomonas putida* and *Saccharomyces cervuisiae, Saccharopolyspora spinosa* and *Zymomonas mobilis*. Particularly good results have been achieved with *E. coli, S. cerevisiae* and *Clostridium*. Further *Pseudomonas*, e.g. *P. putida*, are particularly advantageous because of a high resistance against various organic substances.

The micro-organism may be used to produce an organic substance that the wild-type of such micro-organism produces. However, these micro-organisms are also particularly suitable for industrial scale production of various organic substances not naturally produced or only produced at very low levels by the wild-type. Genetic modification for these organisms is well known in the art. The genetically modified micro-organisms can e.g. be produced based on standard genetic and molecular biology techniques that are generally known in the art, e.g. as described in Sambrook, J., and Russell, D. W. "Molecular Cloning: A Laboratory Manual" 3d ed., Cold Spring Harbor Laboratory Press, Cold Spring Harbor, NY, (2001); and F. M. Ausubel et al, eds., "Current protocols in molecular biology", John Wiley and Sons, Inc., New York (1987), and later supplements thereto. Further, properties of a naturally occurring biocatalyst may be improved by biological techniques known to the skilled person in the art, such as e.g. molecular evolution or rational design. Mutants of wild-type biocatalysts can for example be made by modifying the encoding DNA of an organism capable of acting as a biocatalyst or capable of producing a biocatalytic moiety (such as an enzyme) using mutagenesis techniques known to the person skilled in the art (random mutagenesis, site-directed mutagenesis, directed evolution, gene recombination, etc.). In particular the DNA may be modified such that it encodes an enzyme that differs by at least one amino acid from the wild-type enzyme, so that it encodes an enzyme that comprises one or more amino acid substitutions, deletions and/or insertions compared to the wild-type, or such that the mutants combine sequences of two or more parent enzymes or by effecting the expression of the thus modified DNA in a suitable (host) cell. The latter may be achieved by methods known to the skilled person in the art such as codon optimisation or codon pair optimisation, e.g. based on a method as described in WO 2008/000632. WO 2003/010183 discloses a particularly suitable process for the preparation of variant polynucleotides using a combination of mutagenesis of a starting population of polynucleotides and recombination of the mutated polynucleotides.

Further examples of suitable micro-organisms are known from WO 2008/113041 (LS9), WO 2012/024186, WO 2007/139924, U.S. Pat. No. 7,659,097B2 and from Kalscheuer R, Stölting T and Steinbüchel A. 2006. Microdiesel: *Escherichia coli* engineered for fuel production. Microbiology 152: 2529-2536 or in Li Q, Du W and Liu D. 2008. Perspectives of microbial oils for biodiesel production. Applied Microbiology and Biotechnology 80: 749-756 or in Schirmer et al. 2010. Microbial biosynthesis of alkanes. Science 329: 559-562 or in Ladygina et al. 2006. Process Biochemistry 41: 1001-1014. The cells can e.g. be dispersed mono-cellularily or the cells can form flocs which are dispersed in the aqueous phase. Flocculation can be initiated by liquid product recovery phase.

Other suitable biocatalysts, e.g. enzymes, can also be based on known reactions for obtaining a specific organic substance of interest. For various organic substances, exemplary references to suitable biocatalytic systems will be provided below.

The method respectively bioreactor system according to the invention can in principle be employed for any kind of organic substance that can be produced using a biocatalyst, e.g. it can be used for organic substances with a medium solubility in/miscibility with water, such as methanol, ethanol, propanols (in particular n-propanol, isopropanol), butanols (in particular n-butanol, 2-butanol, tert-butanol, butanediol) and other solvents having about the same solubility in/miscibility with water.

The method respectively bioreactor system is particularly advantageous for the production/recovery of an organic substance that are not miscible with water in any ratio in water; an organic substance that has an intermediate or poor solubility in water under the conditions existing in the reaction section; or an organic substance that is toxic to the biocatalyst (inhibiting the biocatalyst substantially) under the conditions existing in the reaction section. As a rule of thumb, in practice, solubilities in water at 25° C. can be taken to determine whether an organic substance has intermediate or poor solubility. An organic substance with an intermediate solubility typically has a solubility of 35 parts per million by weight (ppmw) to about 100 g/l, in particular 35 ppmw to about 50 g/l, more in particular 35 ppmw to about 1 g/l. A poor solubility is in particular a solubility of less than 35 ppmw, preferably of about 0.5 ppmw to less than 35 ppmw, more preferably of about 1 ppmw to about 30 ppmw, in particular about 4 ppmw to about 25 ppmw. The invention is further particularly advantageous for producing organic substances having a product titre of about 0.1 to 10 g/L based on effective toxicity (e.g. monoterpenes). At such titre the total water content in relation to product is creating need for extra energy/processing equipment further downstream as all of this water needs be processed.

Suitable biocatalytic reaction conditions for the production of a specific organic substance can be based on common general knowledge, in combination with one or more other publications cited in the present disclosure (including citations in said other publications) and/or the remainder of the present disclosure, e.g. the Examples.

Preferred organic substances produced/recovered in accordance with the invention include the following:

Hydrocarbons, in particular C5-C25, more in particular C8-C20, even more in particular C10-C20, which may be aliphatic or aromatic, saturated (e.g. alkanes) or non-saturated (e.g. terpenes), linear or branched; more preferably hydrocarbons selected from the group consisting of monoterpenes, and, sesquiterpenes and diterpenes, hemiterpenes, triterpenes, tetraterpenes and polyterpene. Suitable biocatalysts and bioreaction conditions may e.g. be based on WO 2012/17712 or US 2015/0259705, Isoprenoids (terpenoids), in particular C5-C25, more in particular C8-C20, even more in particular C10-C20. Examples of publications describing Suitable biocatalysts and bioreaction conditions may e.g. be based on WO 2012/17712 or US 2015/0259705.

Organic acids (carboxylic acids), typically having at least 3 carbon atoms (C3); preferably the carboxylic acid is a C5-C24 carboxylic acid; more preferably a C8-C22 carboxylic acid, in particular a C12-C20 carboxylic acid. The carboxylic acid has at least one carboxylic acid functionality, but can have more, in particular 2 or 3, or combined with one or two different functionality like a carboxylates with a double bond. Specific examples of carboxylic acids lactic acid, succinic acid, citric acid, adipic acid. Of particular interest are fatty acids, such as C5-C10 fatty acids that are toxic (chain elongation process. The organic acid can be cyclic or non-cyclic. A suitable biocatalyst or reaction conditions can e.g. be based on WO 2014/129898, WO 2011/031146, or WO 2010/104390.

Alcohols; the alcohol may be an alcohol naturally produced by a yeast, e.g. a *Saccharomyces*, such as ethanol or a fusel alcohol; preferably the alcohol has at least 4 carbon atoms (C4), preferably 4-26, in particular 5-16, more in particular 6-12. The alcohol can be a mono-alcohol, a diol or a polyol. Of specific interest is, butanediol. Also of specific interest are phenols. Also of specific interest are fatty alcohols, i.e. primary branched or straight-chain alcohols having at least 4 carbons, of which n-butanol, 1-dodecanol (lauryl alcohol), 1-octadecanol (stearyl alcohol) cis-9-octadecen-1-ol (oleyl alcohol) and Z11-hexadecene-1-ol (a pheromone, which is suitable for use in pest control) are preferred examples. A suitable biocatalyst or reaction conditions can e.g. be based on WO 2014/129898' or WO 2016/207339.

Mono or polyphenolic compounds, in particular those which are naturally synthesized by plants from the amino acids phenylalanine and tyrosine; preferably selected from the group consisting of flavonoids, iso-flavonoids, coumarins, aurones, stilbenes, catechin, lignols; examples are resveratrol, vanillin, β-carotene, Catechol, Carvacrol, Sesamol. A suitable biocatalyst or reaction conditions can e.g. be based on a plant wherein the compound is naturally produced.

Cannabinoids, e.g. selected from the group of tetrahydrocannabinolic acid (THC-acid), tetrahydrocannabinol (THC), cannabidiol (CBD), cannabidiolic acid, cannabinol, cannabigerol, cannabichromene, cannabicyclol, cannabivarin, tetrahydrocannabivarin, cannabidivarin and cannabichromevarin. A preferred cannabinoid is CBD. Further, THC-acid and THC are of particular interest. The cannabinoid can be a suitable component for a medical composition or a precursor for a medical compound. Suitable fermentative conditions may e.g. be based on WO2019046941A1 or WO2019014490A1.

Ketones; the ketone usually has at least 3 carbon atoms, preferably 5-16 carbon atoms, in particular 6-12. Of specific interest is acetone. The ketone may, e.g., be a ketone naturally produced by a yeast, e.g. *Saccharomyces*.

Aldehydes; the aldehyde usually has at least 3 carbon atoms, preferably 5-16 carbon atoms, in particular 6-12. The aldehyde may, e.g., be a aldehyde naturally produced by a yeast, e.g. *Saccharomyces*. A preferred aldehyde is (Z)-1 1-hexadecenal, which may be used as a pheromone, in an advantageous embodiment in combination with Z11-hexadecene-1-ol. The fermentative production may e.g. be based on WO 2016/207339.

Cyclic carboxylic esters; Cyclic carboxylic esters typically have at least 2 carbon atoms, in particular 4-12; preferred are lactones, more preferred is a lactone selected from the group of alpha-acetolactone, beta-propiolactone, gamma-butyrolactone, delta-valerolactone and epsilon-caprolactone.

Non-cyclic esters; typically the non-cyclic ester have at least 3 carbon atoms, in particular 5-20 carbon atoms, more in particular 6-12 carbon atoms; preferred esters included aroma's, e.g. as obtainable from fruits, beer or wine; esters may be formed naturally in a reaction section wherein a yeast, e.g. a *Saccharomyces* is used as a biocatalyst. Esters can also be useful for providing a pheromone (or pheromone composition), e.g. for use in pest control. A preferred example thereof is (Z)-1 1-hexadecen-1-yl acetate, which may be used in combination with Z)-1 1-hexadecenal, and/or Z11-hexadecene-1-ol; it may also be produced using a method based on WO 2016/207339.

Dyes/colours/pigments and precursors thereof. The dye/colour/pigment or precursor can be any natural dye/colour/pigment compound or combination of compounds, e.g. from a plant or animal, and which compound(s) can be expressed in a microorganism. The dye can for instance be a basic dye, e.g. safranin, basic fuchsin, crystal violet, methylene blue; an acidic dye, e.g. eosin, acid fuchsin or congo red; a food dye, preferably a natural food dye, e.g. a carotenoid, chlorophyllin, an anthocyanin, betanin, annatto, carmine, lycopene or genipin Of specific interest are aromatic cyclic carboxylic acid dyes. In a specific embodiment, the dye/colour/pigment is an actinorhodin or derivative thereof, The fermentative production of a dye/colour/pigment can for instance be based on WO2018138089A1, on Bystrykh Journal of bacteriology vol 178, No 8 (April 1996), p 2238-2244 or on Kanchan Heer and Somesh Sharma (2017): Microbial Pigments As A Natural Color: A Review. In IJPSR vol. 8, issue 5. Pp. 1913-1922.

Pheromones, preferably for use in pest control, e.g. as attractants or repellents of insects or other vermin. Preferred pheromones are selected from the group of Z)-1 1-hexadecen-1-yl acetate, Z)-1 1-hexadecenal, Z11-hexadecene-1-ol (see above) or from the group of spinosyns, in particular from. spinosyn A, D, J and L. The fermentative production of spinosynes can e.g. be based on WO 2016/207339 A1 or WO/2017/087846.

Lipids in particular glycerides, glycolipids, phospholipids; preferred lipids are triglycerides, in particular triglycerides of C4-C24 fatty acids.

Amines; of specific interest are diamines, e.g. 1,6-diaminohexane.

Amino acids; the amino acid can be a proteinogenic amino acid, which may be naturally produced by a living cell, in particular a micro-organism, although the cell may also be genetically modified. It is also possible to produce non-proteinogenic amino acids, which may be produced naturally or after genetic modification. An example of a non-proteinogenic amino acid is 6-aminocaproic acid, which can e.g. be used for the production of caprolactam (for use in the production of polyamides). Biocatalytic production thereof is e.g. described in WO 2011/031146, WO 2011/031146, WO 2010/104390 or EP-A 2252577.

Peptides; the peptide may be naturally produced by a living cell, in particular a micro-organism, although the cell may also be genetically modified.

Hydrocarbons and isoprenoids are of specific interest with respect to a method according to the invention. In a particularly preferred method of the invention, the organic substance is selected from the group consisting farnesene, humulene, abietadiene, amorphadiene, carene, α-famesene, β-farnesene, farnesol, geraniol, geranylgeraniol, isoprene, linalool, limonene, myrcene, nerolidol, ocimene, patchoulol, β-pinene, sabinene, γ-terpinene, terpindene and valencene.

Suitable substrates can also be based on common general knowledge, dependent on the organic substance of interest. In general, when using a living cell as a biocatalyst, a carbohydrate is suitable. Thus, in a preferred embodiment, the substrate comprises a carbohydrate. The carbohydrate is preferably a saccharide, such as a sugar, a starch, cellulose, lignocellulose or a hydrolysate of starch cellulose or lignocellulose. As an preferred alternative to carbohydrate, or additionally, a CO containing gas can be used, in particular a syngas, e.g. from gas stream off gas, cracker off gas.

In a specifically preferred embodiment, the substrate or part thereof is of a bio-based material, in particular a second-generation bio-based feed stock, such as an agro/forestry residual, a hydrolysate thereof or a gasified form thereof (e.g. syngas).

Dependent on the biocatalyst and intended product to be produced, other examples of suitable substrates include glycerol, low cost biofuels (methanol, ethanol and the like), and syngas.

A method according to the invention is carried out using a single apparatus comprising both a reaction section, wherein the organic substance is biocatalytically produced and a separation section wherein the recovery phase comprising produced organic substance is separated from the remainder of the reaction mixture. The reaction section (11) and the separation section (9) are separate compartments, usually present in a single housing; the housing can be constructed of more than one part though. Thus, the reaction section (11) and the separation section (9) form a single device or part of a single device, which may also be referred to as an integrated bioreactor, containing a reaction compartment and separate therefrom a separation compartment.

Typically, the separator section can be controlled separately from the reaction section. For example, the separator can be heated in order to increase coalescence of droplets or the separator can be aerated with a gas flow in order to maintain the cells alive, if the biocatalyst comprises living cells that require or benefit from oxygen. Additional product recovery phase can be added to the separation compartment to extract further produced organic substance from the organic phase, improving the product recovery and/or phase separation.

Typically, at least part of the remainder of the reaction mixture from which recovery phase comprising produced organic substance has been removed (an aqueous fluid, typically comprising biocatalyst if the biocatalyst is dispersed or dissolved in the aqueous fluid) is recycled to the reaction section. Further, in order to avoid excessive build up of component(s), such as undesired side-products, components from the substrate or biocatalyst (e.g. living cells), at least part of the aqueous phase in the apparatus may be withdrawn from the apparatus (so called 'bleeding'). Thus, usually a bleed-provision (4) is present in the apparatus, i.e. an outlet from which the aqueous phase can be withdrawn. Usually such provision is present at a position allowing withdrawal the remainder of the reaction mixture from which recovery phase comprising produced organic substance has been removed (as shown in FIG. 1). This is typically the outlet for the bleed is combined with a recycle outlet. Optionally an outlet from the separation section (9) at a position suitable to withdraw aqueous phase (i.e. below the interface between aqueous phase and recovery phase in a system wherein they are separated by a density differences wherein separate layers are formed, in case the recovery phase has a lower density than the aqueous phase, respectively above said interface if the recovery phase has a higher density). In principle it is also possible to have a bleed provision in the separation section, but this is considered less efficient with respect to product recovery (given the presence of produced organic substance in the reaction mixture inside the reaction section). A high cell retention can be achieved with a substrate solution that has a high concentration and a low bleed rate (or none at all) and/or little harvest of aqueous phase (high product recovery rate).

Optionally the apparatus is connected to one or more further apparatuses, together forming a more extended bioreactor system. For instance, it is possible to have the inlet (1) for substrate (and nutrient, if living cells are used) into the reaction section (11) connected to a preceding bioreactor, wherein already organic substance is produced. Accordingly, in a specific embodiment, the bioreactor system comprises a further bioreactor vessel having an outlet for a fluid (comprising substrate and optionally biocatalyst and/or produced organic substance) that is connected via a fluid channel with the feed inlet (1) of the reaction compartment (1) of said apparatus. Such bioreactor is particularly advantageous in case the method is a fermentative method. The bioreactor preceding the apparatus, such as a pre-fermenter, comprising the reaction section (11) and separation section (9) can be used to keep the concentration of micro-organisms in the reaction section (11) of the apparatus at an advantageous level, especially when producing the organic substance anaerobically, after all, under anaerobic conditions growth/proliferation of the cells is limited. In such case, the bioreactor is also referred to in the art as an inoculation reactor. The bioreactor preceding the apparatus comprising the reaction section (11) and separation section (9) can also be a bioreactor already used for industrial scale production of an organic substance. The substrate and/or nutrient needed for the biocatalyst in the reaction section (11) can, in principle be supplied solely via the preceding bioreactor, but advantageously, additional feed is provided separate from the preceding bioreactor. One may further introduce at least part of the product recovery phase, especially a liquid, to the preceding bioreactor. This is particularly advantageous in a fermentative method. This allows the cells to get used to the presence of the recovery phase and to extract product.

An exchange rate between the two reactors is advantageously chosen in such a way that the productivity of the proceeding reactor is optimized by balancing the residence time of the product recovery phase in the preceding reactor and the overall recovery of the product recovery phase in the separation section.

The productivity of the preceding reactor can be improved by connecting the separation section to existing reactors.

Further, one or more streams leaving the apparatus may be further processed; in particular a further apparatus may be used to separate organic substance from the organic recovery phase. Suitable apparatuses, separation conditions and further purification steps or other processing steps may be based on known technology for a particular organic substance of interest. Organic recovery phase from which organic substance has been removed can be recycled.

A particularly suitable apparatus for use in a method according to the invention is a bioreactor system as schematically shown in FIG. 1. The reaction compartment (11) is situated in a lower part of the apparatus and the separator compartment (9) is situated in an upper part of the apparatus, both in the same housing (12). A riser (7) defines a channel adjacent to the upper part of the reaction compartment (11). The riser is adapted to allow fluid from the reaction compartment (11) to flow upward. A downcomer (8) defining a channel between the outlet side of the riser (7) and the inlet side of the separator compartment (9) is adapted to allow (non-gaseous) fluid leaving the riser (7) to flow downward into the separator compartment (9). The reaction compartment (11) comprises an agitator (13), preferably a stirrer but other known means to cause turbulent flows may also be used. The feed inlet (1) for a substrate (an other substances such as nutrient) for use in the production of the substance is provided. The inlet (5) for a product recovery phase can be the same inlet as inlet (1) for the substrate, but is preferably a separate inlet, which is more preferably positioned closer to the bottom of the reaction compartment than the feed inlet (1) for substrate. Preferably an inlet (6) is present for a gas phase, preferably a sparger. This inlet (6) is typically positioned closer to the bottom of the reaction compartment than the feed inlet (1). The positioning of the inlet (6) for gas phase in a lower part of the separation section, in particular at or near the bottom of the separation section, is advantageous because in that way, the gas bubbles are better mixed in the liquid. Further, when an agitator is present, such as a stirring device, the inlet (6) is typically placed below the agitator, This is also advantageous for distributing the gas bubbles. Further, the gas bubbles will be smaller due to the power input by the agitator, which is in particular desired in a system operating under aerobic conditions, as smaller gas bubbles provide higher oxygen transfer.

The separator compartment (9) comprises an outlet for product recovery phase (3), typically positioned closer to the top of the separator compartment (2) than the outlet end of the downcomer (9). Generally, the outlet for product recovery phase (3) is positioned at the middle part or top part of the separator compartment, as the lighter phase rises to the top of the liquid level.

The outlet (3) can be connected in fluid communication with a further processing apparatus, such as an apparatus to separate the organic substance of interest from the recovery phase (not shown). Preferably, a recycle provision (10) is present for recycling fluid taken from a part of the separator compartment (9) to the reaction section. This fluid is typically an aqueous phase, wherein biocatalyst is dispersed or dissolved (if a dispersed or dissolved biocatalyst is used in the production of the organic substance). If a gas phase inlet (2) is present in the separation compartment, preferably the recycle provision is adapted to withdraw fluid from the separation compartment below the inlet (2) for the gas phase to the separation compartment (9). The apparatus usually has an outlet or outlets for gas phase (15, 16) introduced into the apparatus via the inlet or inlets for gas phase (2, 6). A gas outlet (15) is usually present adapted to allow gas produced or introduced in the reaction section to be withdrawn. Such outlet is conveniently positioned to withdraw gas from a headspace above the reaction section, in particular above the riser. A gas outlet (16) is usually present adapted to allow gas introduced in the separation section (via a gas inlet (2)) or gas that has not been removed from the reaction mixture prior to proceeding into the separation section (if any) to be withdrawn. Such outlet is conveniently positioned to withdraw gas from a headspace above the separation section.

Good results have in particular been achieved with a bioreactor system, wherein the reaction compartment (11) is positioned below the separator compartment (9) are on opposite sides of the partition (14) and the recycle provision (10) comprises one or more openings in the partition. Typically, both compartments (9) and (11) share the partition (14). Herein the partition functions as a floor for one and as a ceiling for the other. Typically one or more openings are present at or near the lowest point of the partition, to allow recycle of aqueous phase to the reaction compartment. The partition (14) may be tilted. Usually the partition (14) is at an angle of 90° or more with the outflow-direction of fluid from the downcomer (9). If the direction of the flow into the separation section wherein recovery phase is separated from aqueous phase is perpendicular or less (at 90° or less) to the partition, this can have the effect of an increasing Reynolds number (Re), a measure for flow patterns, generally known in the art of fluid mechanics. I.e. turbulences may more easily be introduced into the flow, especially at a high flow velocity and/or low viscosity of the fluid introduced into the separation section. A smaller angle may create a dead end in the separation section. A small increase in the angel already has a positive effect on maintaining laminar flow. Usually, the angle relative to the flow out of the downcomer and/or relative to the vertical axis is in the range of 90-120°.

The riser, downcomer, separation compartment can be incorporated into a an existing bioreactor, e.g. mounted via flanges to the bioreactor (forming the reaction compartment). This separator unit can be just as wide as the bioreactor. However, the separator unit can be made wider if higher separation capacity is required.

The recirculation compartment enables the flow of non-harvested liquid towards the fermentation compartment and can be implemented as external tube or tubes, internal tube or tubes, as an alternative to or in addition to openings in the partition (14) between the separation and reaction compartments.

In an advantageous embodiment, the separator section comprises an inlet (2) for a gas phase, preferably a micro-bubble sparger which is typically positioned closer to the bottom of the separator section (2) than the outlet end of the downcomer (9). The gas bubbles are introduced at a relatively low flow rate, thereby not causing turbulent flow conditions in the separator section. For the gas bubble induced oil recovery, the optimal value of the superficial gas velocity in the separation section is typically significantly lower than the optimal value in the reaction section. Usually, if gas is supplied, the superficial gas velocity in the separation section is in the range of 0.01-2 cm/s. preferably 0.05 to 1.5 cm/s, more preferably e.g. 0.1-1.0 cm/s and for the fermentation; the superficial gas velocity advantageously is at least about one order of magnitude higher. Usually, the superficial gas velocity in the reaction section is at least 1.0 cm/s, preferably in the range of 1.5-30 cm/s, more preferably in the range of 2.0-15 cm/s. Due to the large difference in the required gas flows for reaction (fermentation) and separation, the multi-compartment design in accordance with the invention is required to be able to integrate fermentation and separation in a single piece of equipment, to avoid too high a gas flow in the separation section, which may disturb the flow conditions in the separation section, and thereby adversely affect the separation efficiency or capacity.

Further, the gas bubbles typically have a Sauter mean diameter of 4 mm or less, in particular of 0.5-4.0 mm. more in particular of, 1.0 mm-3.5 mm. The introduction of the gas bubbles in the separation section contributes to coalescence of droplets/particles of the recovery phase and/or contributes to an upward motion of the droplets/particles, thereby having a positive effect on separation effectivity and/or separation rate.

The use of gas flows in at least one, and preferably in both the reaction section (from external gas introduced via a gas inlet (6) and/or internally produced gas) and the separation section (from external gas introduced via a gas inlet (2)) is beneficial with the aim of providing simple and cheap process technology, especially when a liquid recovery phase is used. The circulation flow between the reaction compartment and the separation compartment is thus induced in a simple way by a difference in density between the reaction section and the separation section. A difference in gas holdup is advantageously created in an apparatus with a riser by the difference between fermentation/riser and downcomer. There is a lot of gas in the riser but no (or almost none) gas in the downcomer. In gas lift reactors, for example, this density difference results in an upwards liquid flow in the riser and a downward liquid flow, creating a circulation flow in the reactor. The same principle can be used in the integrated reactor (apparatus) in accordance with the invention to create the circulation flow between the reaction compartment and the separation compartment, wherein recovery phase comprising the produced organic substance is recovered from the reaction mixture. When the fluid reaction mixture flows from the reaction compartment to the separation compartment, the gas bubbles are removed to obtain a quiescent environment in which the separation can take place. Removal takes place by allowing the bubbles to escape via the fluid surface above the reaction section (the fluid surface of the riser and of the downcomer, if present). The gas flow in the reaction compartment is preferably led out of the reaction section through a riser, typically a funnel structure or a cylindrical structure, where the superficial gas velocity is increased, further due to the smaller cross sectional area compared to the (maximum) cross sectional area in the reaction compartment. The high superficial gas velocity results in a high gas hold up, leading to a low overall density of the liquid/gas mixture in the riser compared to the mixture in the downcomer and in the separation compartment. The density difference between the two compartments causes a difference in hydrostatic pressure between the separation compartment and the reaction compartment at a certain height. At the recycle provision in the partition separating the reaction compartment and the separation compartment from each other, the difference in hydrostatic pressures between the separation section-side of the recycle provision and the reaction section-side of the recycle provision will induce a fluid flow from the separation compartment to the reaction compartment. In a preferred embodiment, the recycle provision comprises one or more openings in the partition between separation section and reaction section, in particular a plurality of circular or elongated holes, e.g. slits. In a further preferred embodiment, the recycle provision comprises one or more tubes or pipes adapted to recycle the fluid from the separation section to the reaction section. The size of the circulation flow can be set by several controllable operating parameters (e.g. fraction of product recovery phase, gas flows) and the geometry of the reactor, thus enabling operational control of the overall liquid residence times. So the gas injection fulfils several functions that is optimizable for an essentially continuous process.

The use of the gas injection to recirculate aqueous fluid comprising biocatalyst dispersed therein is also advantageous in that the biocatalyst is not exposed to additional shear stress through pumps or blocking membranes used for biocatalyst retention. This is particularly advantageous when using living cells as a biocatalyst, but undesired shear stress and blocking can also be a problem when using, e.g. an immobilised enzyme on a carrier or biocatalytic cell material of lysed cells. Further, the use of the gas injection instead of mechanical pumps adds to simplicity of the system; no additional moving parts are needed for the recycling, but can be included if desired.

The bioreactor system according to the invention is in particular suitable for a method wherein the recovery phase has a lower density than the aqueous phase. Thus, separation can be achieved by causing the recovery phase to form a layer on top of the aqueous phase.

The dimensions of the apparatus and parts thereof can be chosen widely, dependent on the desired scale of production. The skilled person will be able to design the apparatus based on the information given herein, including the cited references and common general knowledge and optionally some routine calculation and/or testing work. Some specific considerations with respect to preferred dimensions when designing a specific reactor are:

The height riser: typically depends on the superficial gas velocity used. Skilled person can calculate this.

The height of the downcomer is preferably at least 0.8 m

Diameter downcomer, the diameter is preferably at least 10× times bigger than the characteristic length of the gas bubbles that have to be removed In a specific embodiment, the separation section is overhanging (wider than reaction section Some further considerations regarding preferred features during operation of a method according to the invention:

Pressure difference is caused by density difference due to gas injection; the skilled person can calculate this)

The recirculation velocity can be calculated from the pressure difference (skilled person can calculate this having knowledge about the friction in the used system. Friction can be determined by a skilled person)

Gas flow can be determined from the superficial gas velocity (gas velocity range was mentioned above)

Temperature depends on microorganism used

Liquid product recovery phase density: lower than aqueous phase; if aqueous phase is only water then below 1000 kg/m$^3$.

The invention further relates to a method for isolating a biocatalytically produced organic substance from a liquid product recovery phase that has been used to extract the biocatalytically produced organic substance from a reaction medium, in particular an aqueous reaction medium, wherein the organic substance has been produced. In a preferred embodiment, the recovery phase is a recovery phase obtained in a method for recovering a biocatalytically produced organic substance from a reaction mixture according to the present invention. In a further preferred embodiment the organic substance has been produced by a different method, notably a method described in the prior art cited herein, which is incorporated by reference with respect its disclosure of fermentation processes and processes for the recovery of fermentatively produced organic substances.

As has been described above, various methods have been proposed to recover biocatalytically, in particular fermentatively produced organic substances, from a reaction medium, such as a fermentation mixture. For hydrophobic organic substances, such as hydrocarbons and lipids, methods can be used that rely on the low water-miscibility of the lipids or hydrocarbon with the aqueous medium. Extractive techniques are also a known possibility. E.g., U.S. Pat. No. 5,628,906 describes an extraction process which comprises adding a primary solvent to a first solution containing a solute (e.g. fermentatively produced substance) in a native solvent (e.g. a fermentation broth) to be extracted from the solution in an amount sufficient to form a single phase comprising the first solution, solute and the primary solvent. Thereafter, a modifier is added to reduce the miscibility of the primary solvent with the native solvent so as to form an immiscible mixture of two phases, wherein one phase is rich in solute and primary solvent. Thereafter, the solute is separated from the primary solvent. The described recovery method is not suitable to be implemented in a method for recovering a biocatalytically produced organic substance from a reaction mixture in accordance with the present invention, because simultaneous production and recovery is not feasible on the basis of its disclosure. Further drawbacks are added complexity due to the need to add the modifier, which may also be toxic to the micro-organism, It is further apparent that recovery rates will be relatively low, and there is no matching of ISPR and SC.

The extraction of the produced organic substance can be done by liquids (liquid product recovery phases) that form a separate phase when contacted with the reaction medium. In choosing the product recovery phase physico-chemical considerations, notably the solubility/miscibility of the product recovery phase in the reaction medium (the lower the better) and the affinity of the produced substance of interest for the product recovery phase (which should be higher than the affinity for the aqueous phase, as expressed by a partitioning coefficient>1) play an important role. Further, one should take into consideration possible adverse affects of the product recovery phase on the biocatalyst, with which the product recovery phase can come into contact. Toxic product recovery phases should generally be avoided, as this limits the possibility to re-use the biocatalyst. Moreover, in systems wherein product recovery phase is added to the reaction mixture whilst the reaction proceeds (so called reactive-extraction systems), inhibiting effects of the recovery phase on the biocatalyst are detrimental to production rate. Product recovery phases that are conventionally used in the art have a boiling point lower than the boiling point of water. A reason to use such product recovery phases resides in problems in down stream processing when using higher boiling product recovery phases, such as organic compounds like fatty oils, waxes, hydrocarbons and alcohols of sufficient carbon length all with boiling points exceeding 100° C. Especially in combination with non-volatile products this means product recovery form the extractive phase can't be carried out directly by evaporation/distillation.

The present inventors realized though that a drawback of using product recovery phase with a relatively low boiling point, in particular a lower boiling point than the reaction medium, typically an aqueous medium, is vaporization of the product recovery phase, which can even be further promoted when introduced in a reaction system that is supplied with gas, e.g. air or oxygen in case of an aerobic system or a gas-lift reactor or the like.

A drawback is also that low boiling point solvents (low molecular weight or volatile due molecular composition is also that these solvents tend to be aqueous soluble.

The inventors found a way to employ a high-boiling non aqueously soluble/having low aqueous solubility (preferably <1 g/L) recovery phase, at least at the temperature(s) at which the recovery phase is contacted with the reaction medium to extract the organic substance from the reaction medium), whilst addressing one or more of the drawbacks mentioned above. High-boiling, as used herein means a boiling point of 100° C. or more at 1 bara.

Accordingly the invention further relates to a method for isolating a biocatalytically produced organic substance from a liquid product recovery phase, comprising a first extraction, wherein the organic substance is extracted from an aqueous or non-aqueous reaction medium—wherein the organic substance has been produced in the presence of biocatalyst catalyzing the production of the organic substance—into the liquid product recovery phase, which liquid recovery phase has a boiling point of at least 100° C.;

a separation of the liquid product recovery phase, containing the organic substance from the reaction medium;

a second extraction, wherein the produced organic substance is extracted from the product recovery phase into an extraction liquid (the so called back extraction liquid), different from the product recovery phase;

a separation of said extraction liquid from the product recovery phase; and an isolation of the organic substance from said extraction liquid.

Volatile products can be easily removed from the high boiling point solvent. Products with higher boiling point need other strategies afterwards, e.g. back-extraction.

Further, considering a conventional extractive fermentation without removal of the organic phase, one has to process the whole broth and if there is a solvent with high boiling point (higher than water), it would mean a lot of energy. However, this can be avoided with our technology. So one can recover the product containing phase with little or no water in it and then solvents with high boiling points become attractive.

General considerations with respect to the product recovery phase, the produced organic substance and other aspect are as described in the remainder of the present disclosure, with the proviso that the product recovery phase is a liquid at the temperature in the reactor compartment wherein the organic substance is used, and has a boiling point (at 1 bara (atmospheric pressure)) of 100° C. or more, generally in the range of 120-500° C. Usually, the boiling point (at 1 bara (atmospheric pressure)) of the liquid recovery phase in the method for isolating the biocatalycally produced organic substance from the liquid recovery phase is at least 130° C., preferably at least 150° C., in particular at least 250° C. In a specific embodiment it is about 300° C. or more. The boiling point (at 1 bara (atmospheric pressure)) of the liquid recovery phase preferably is about 400 the boiling point of the liquid recovery phase or less, in particular about 380° C. or less. In a specific embodiment the boiling point (at 1 bara (atmospheric pressure)) of the liquid recovery phase is 300° C. or less, e.g. 250° C. or less, in particular of 150-250° C. Amongst others, good results have been achieved with a liquid product recovery phase selected from the group consisting of oleyl alcohol, dodecane, castor oil and soybean oil.

Usually, the liquid product recovery phase at least substantially consists of one or more organic compounds, Usually, the back-extraction liquid at least substantially consists of one or more organic compounds, Further, the product recovery phase is typically chosen in combination with a back-extraction liquid to have an operation window (temperature 'T', pressure p and fraction 'x' of the total volume of product recovery phase and back extraction liquid) at which they form separate phases, and preferably also an operation window (T, p, x) at which they form a single liquid phase. A preferred example thereof is the combination undecanol (product recovery phase) and ethanol (back extraction liquid). The skilled person will be able to choose other combinations based on the information disclosed herein and phase diagrams, as generally known in the art. The back extraction liquid typically has a boiling point lower than water (less than 100° c. at 1 bara).

Alternatively, or in addition a combination may be chosen that has an operating window in terms of melting/solidifying behaviour: i.e. having different melting points in mixture, The presence of an operation window at which phase separation occurs allows back-extraction of product from the high boiling product recovery phase to the (low boiling) back-extraction liquid. After liquid-liquid separation (e.g. by centrifugation) product enriched back-extraction liquid is obtained. The biocatalytically produced product can then by isolated from the back-extraction liquid, based on known technology. E.g. it can be isolated by vapour phase formation, with the back-extraction liquid as the vapour if it has a lower boiling point than the biocatalytically produced product of interest.

An additional benefit of this extraction-back extraction approach is that the affinity of contamination species for the back-extraction liquid can be chosen so it does not enrich. Higher product purity can then also be obtained.

The extraction—back extraction process of the invention also allows the use of extraction liquids that cannot readily be applied to the fermentation system (due to e.g. aqueous solubility and related solvent losses, due to a high vapour pressure, or due to toxicity for the fermentation). However, the high boiling point product recovery phase containing product recovered from the fermentation, at least when recovered by a method according to the present invention, has concentrated the product to an organic phase mostly free of aqueous solution. It can thus be treated with low-boiling organic solvent for back-extraction, while not being susceptible to the requirement of evaporating water.

Especially a temperature effect can be used for chemicals known to have eutectic properties as entropic effects can be very strong. For eutectic chemicals the melting point of the mixture is lower than the melting point of the individual components (e.g. dodecanol and undecanol mixture also enabling liquid-solid phase separation of the solvent and back-extracting solvent.

Specific embodiments of the process for isolating the biocatalytically produced substance in particular comprise one or more of the following the product recovery phase and the extraction liquid are brought in contact with each other at a temperature and in a ratio at which they form mixed phase, after which the temperature is changed to induce phase separation, whereby an extraction liquid phase is obtained enriched in the biocatalytically produced organic substance.
  the extraction liquid has a lower boiling point than the product recovery phase, and wherein the organic substance is isolated from the extraction liquid by distillation.
  organic substance is isolated by precipitation, in particular by crystallization, e.g. by reducing the temperature to a temperature at which the organic substance solidifies, whilst the extraction liquid remains liquid.
  the product recovery phase is selected from the group consisting of fatty acids, waxes, primary alcohols having a boiling point of 100° C. or more and/or the extraction liquid is selected from the group consisting of alcohols (mono-, di- or polyol), ethers, esters, which product recovery phase or extraction liquid may be aromatic or aliphatic.

the first extraction comprises the use of a method for recovering an organic substance according to the invention the biocatalyst and/or organic substance are as defined in any of the claims 1-17 or as described elsewhere in the present disclosure.

Amongst others, good results are obtained with a product recovery phase selected from decanol, oleyl alcohol, soybean oil and castor oil in the first extraction and using a volatile solvent, such as ethanol, butyl-acetate or a solvent having at least about the same volatility as ethanol as the back-extracting liquid for the second extraction. In a preferred embodiment of the process for isolating the biocatalytically produced organic substance, the organic substance is produced using a biocatalyst in a reaction mixture comprising a continuous aqueous phase, in which the biocatalyst is preferably dispersed or dissolved, which aqueous phase comprises a substrate for the biocatalyst, and wherein further droplets of the liquid product recovery phase are dispersed in the continuous aqueous phase, into which droplets produced substance migrates; and the product recovery phase comprising the produced substance from the aqueous phase and the biocatalyst is separated, wherein the production of the organic substance and the separation of the product recovery phase are carried out in an apparatus comprising a reaction section, containing the reaction mixture wherein the substance is produced, and a separation section wherein the product recovery phase comprising the produced substance is separated from the aqueous phase. Preferably, the process comprises a simultaneous production and separation stage, such as described above for a method for recovering a biocatalytically produced organic substance from a reaction mixture according to the invention; i.e. in a preferred embodiment, a liquid product recovery phase comprising the biocatalytically produced organic substance recovered by a method according the invention is preferably subjected to a process for isolating a biocatalytically produced organic substance from a liquid product recovery phase according to the invention.

The invention will now be illustrated by the following examples.

EXAMPLES

Example 1: Anaerobic Production of ABE (acetone-butanol-ethanol)

ABE (acetone-butanol-ethanol) was catalytically produced by *Clostridia beijerinckii* (NCIMB 8052) using technical oleyl alcohol as the product recovery phase (solvent). The microorganism strain was kindly provided by Food and Biobased Research, Wageningen University and Research Centre. The strain was obtained from the NCIMB collection.

The following medium was prepared for the experiment:

TABLE 1

| Medium prepared for the experiment | |
| --- | --- |
| Solution/medium | Total amount |
| Preculture 1 medium (CM2) | 0.3 kg |
| Preculture 2 medium (CM2) | 3.5 kg |
| Batch medium (CM2) | 70 kg |

TABLE 1-continued

| Medium prepared for the experiment | |
| --- | --- |
| Solution/medium | Total amount |
| Feed medium (glucose, NH$_4$acetate) | 75 kg |
| Yeast extract stock | 0.5 kg |
| Iron sulfate solution (1000X)* | 0.1 kg |
| Oleyl alcohol (technical) | 200 kg |
| Base (2M KOH) | 2 kg |
| Antifoam 204 | 1 kg |

The CM2 medium has the following composition:

TABLE 2

| CM2 medium composition | |
| --- | --- |
| CM2 medium components | Final concentration |
| K$_2$HPO$_4$•3H$_2$O | 0.8 g/L |
| KH$_2$PO$_4$ | 1 g/L |
| NH$_4$acetate | 2.9 g/L |
| p-aminobenzoic acid (PABA) | 0.1 g/L |
| MgSO$_4$•7H$_2$O | 1 g/L |
| FeSO$_4$•7H$_2$O solution (1000X) | 1 mL |
| Antifoam 204 | 7 mL |
| Sterile additions | |
| Glucose | 60 g/L |
| Yeast extract | 2.5 g/L |

The medium was autoclaved at 121° C. for 20 min except for glucose and yeast extract (YE Duchefa Biochemie prod. Y1333.0500) solutions. These solutions were autoclaved separately at 110° C. for 20 min and at 121° C. for 20 min respectively and added sterilely afterwards. The pH of the CM2 medium was adjusted to 6.3. The iron solution was prepared separately as 1000 concentrated solution dissolved in 0.1 M HCl and then, 1 mL of the iron stock solution was added to the rest of the CM2 medium. For medium preparations, it can be also referred to Diallo, M., Simons, A. D., van der Wal, H., Collas, F., Houweling-Tan, B., Kengen, S. W., & López-Contreras, A. M. (2019). L-Rhamnose metabolism in Clostridium beijerinckii strain DSM 6423. Appl. Environ. Microbiol., 85(5), e02656-18.

The feed medium consisted of 330 g/L glucose and 1 g/L NH$_4$acetate that was autoclaved at 110° C. for 20 min and sparged with N$_2$ in order to remove the oxygen. The product recovery phase oleyl alcohol (Chempri, Raamsdonkveer) was not sterilized. The solvent was colored with Oil Red O at a concentration of 75 mg/kg$_{solvent}$.

The 6 anaerobic jars for preculture 1 had each a butyl-rubber on top and an aluminum cap. The jars were filled with 5 mL demi water and flushed with N$_2$ gas for 10 min. Afterwards the jars were filled with 50 mL CM2 medium. Just before inoculation, the jars were flushed with N$_2$ for 10 min again.

6 vials of 1 mL frozen culture stocks were heat shocked for 75 s at 100° C. in a water bath and immediately cooled for 1 min under a running tap. The heat shocked cells were then transferred to the sterile anaerobic jars with 50 mL CM2 medium. A bike valve equipped with a 0.2 μm sterile filter was placed into the rubber cap of the anaerobic jar to release the gases formed during the incubation. Preculture 1 was incubated at 37° C. and 0 rpm for 24 h.

After incubation of preculture 1, 180 mL of preculture 1 was added to 3.32 L CM2 medium in a 3.5 L bioreactor. The anaerobic bioreactor was heated to maintain a temperature of 37° C., flushed with N$_2$ gas and incubated for 24 h without any stirring or pH control.

The integrated bioreactor was prepared as followed: the pH probe was polarized and calibrated offline (2-points calibration with buffer solutions of pH 4.0 and 7.0). An empty sterilization was performed at 125° C. for 30 min. The batch medium (without yeast extract and glucose) was prepared and pumped into the reactor. A full sterilization of the reactor is subsequently performed at 121° C., 20 minutes. Only after full sterilization and cooling of the reactor, the batch sterile solutions (yeast extract and glucose) are pumped into the reactor. Nitrogen gas flowed into the reactor for at least 30 min to make the medium anaerobic. The fermentation controllers were set in the control unit eZ-control. If the pH drops below 5.2 after 24 h after inoculation, the pH is controlled with base. After the batch phase, the stirring speed is increased from 0 rpm to 300 rpm.

The stirring speed was suitable to maintain turbulent flow conditions in the fermentation reactor and D[3,2] at a value in the range of about 10 to about 100 μm.

TABLE 3

| Operation conditions of the experiment during the batch phase and the continuous phase | | |
| --- | --- | --- |
| Parameter | Value | Unit |
| Temperature | 37 | ° C. |
| Vessel pressure | 0.2 | Barg |
| N$_2$ flow | 25-35 | L. min$^{-1}$ |
| pH | 6.3 to 5.2 | — |
| pH control | Only base after 24 h | — |
| Stirring | Batch phase: 0 | rpm |
| | Continuous phase: 250-300 | |
| Anti-Foam cycle | Foam: on contact | Yes |

The batch phase ended 17 h after inoculation when the glucose concentration was close to 0 g/L and the continuous feed of glucose was started at 0.25 kg/h.

The feed rate was adjusted during the continuous phase as following:

TABLE 4

| Adjustments of the feed rate during the continuous phase | |
| --- | --- |
| Time after inoculation [h] | Feed rate [kg/h] |
| 23.0 | 0.4 |
| 24.8 | 1.2 |
| 28.6 | 1.0 |

The feed rate was adjusted because the glucose drop after the batch was almost to 0 g/L. The glucose concentration was increased over 20 g/L. The feed rate was then decreased stepwise to maintain a minimum glucose concentration of 20 g/L.

Moreover, the continuous solvent addition was set to 0.6 kg/h after the end of the batch phase until 24 h after inoculation and set to 1.3 kg/h till the end of the fermentation. The harvest was started 22 h after inoculation. The recirculation loop was opened to the maximum since the beginning of the fermentation. Flow conditions in the separator compartment were kept non-turbulent (laminar flow)

Results and process details are shown in FIGS. 20-27.

Figure 20:
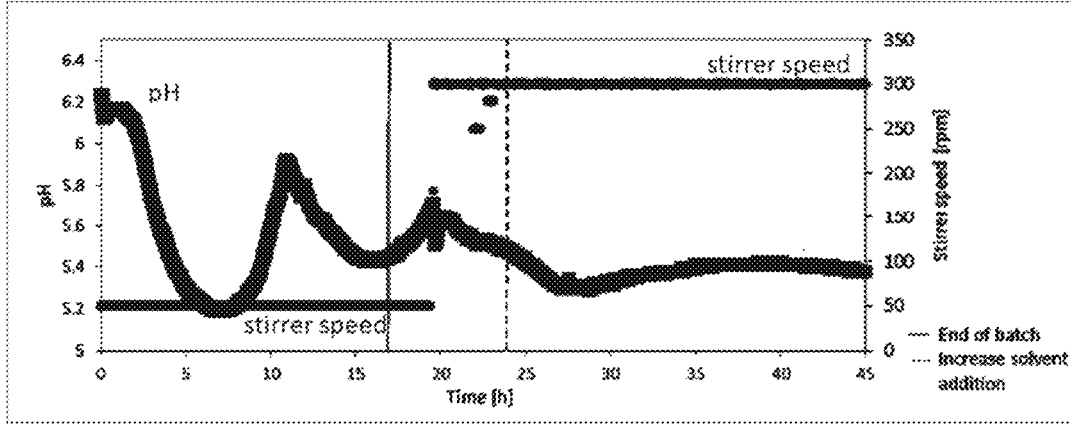
FIG. 20 shows a development of pH during the fermentation.

FIG. 20 shows the development of pH during the fermentation.

Figure 21:
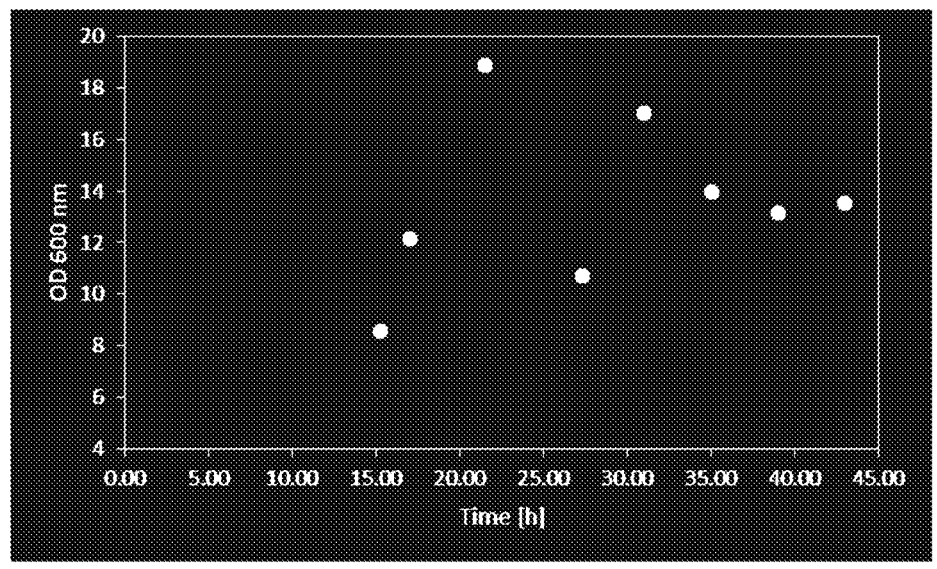
FIG. 21 shows a optical density (OD) values of the batch and continuous phase.

FIG. 21 shows the optical density (OD) values of the batch and continuous phase.

Figure 22:
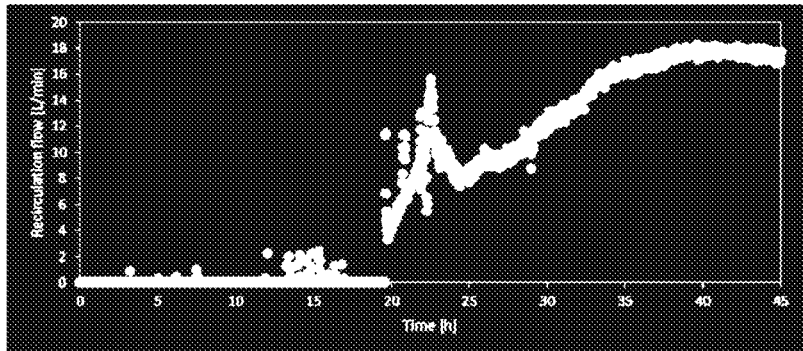
FIG. 22 shows a measured recirculation flow during the batch and continuous phase
Figure 23:
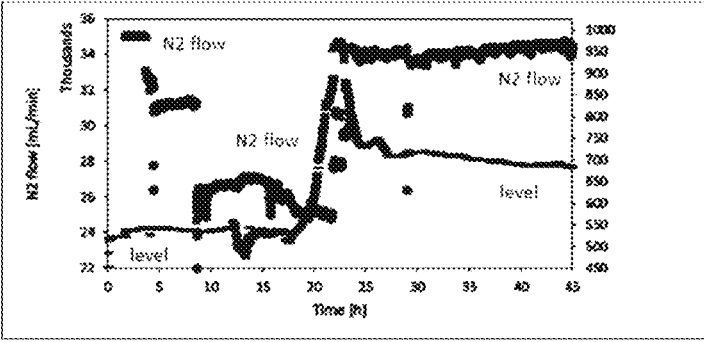
FIG. 23 shows a N₂ gas flow in and liquid level measurement of the separation compartment.

FIG. 22 shows the measured recirculation flow during the batch and continuous phase FIG. 23 shows the N$_2$ gas flow in and liquid level measurement of the separation compartment.

Figure 24:
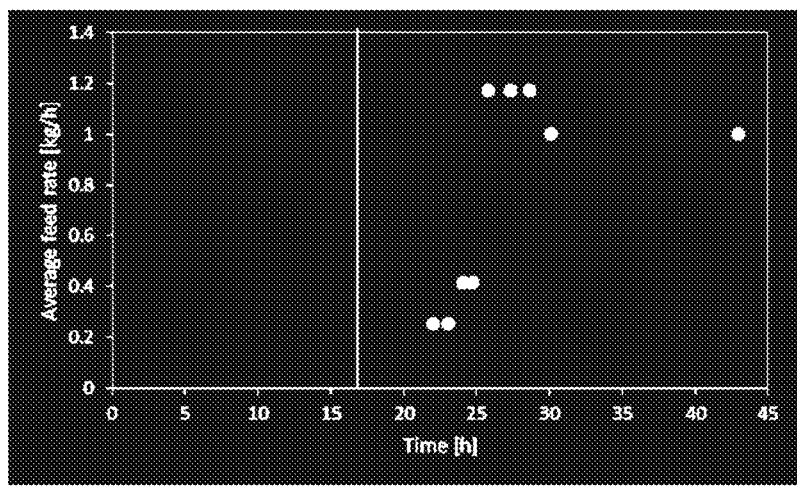
FIG. 24 shows an average feed rate during the continuous phase after the batch ended (vertical black line).

FIG. 24 shows the average feed rate during the continuous phase after the batch ended (black line)

Figure 25:
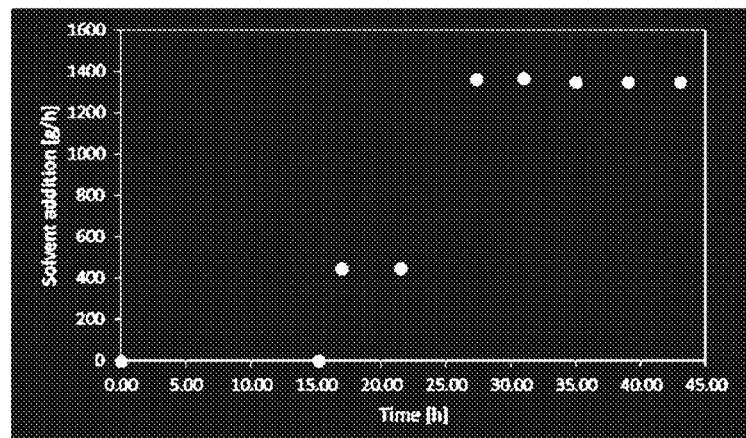
FIG. 25 shows solvent (recovery phase) addition during the continuous phase.

FIG. 25 shows solvent (recovery phase) addition during the continuous phase.

Figure 26:
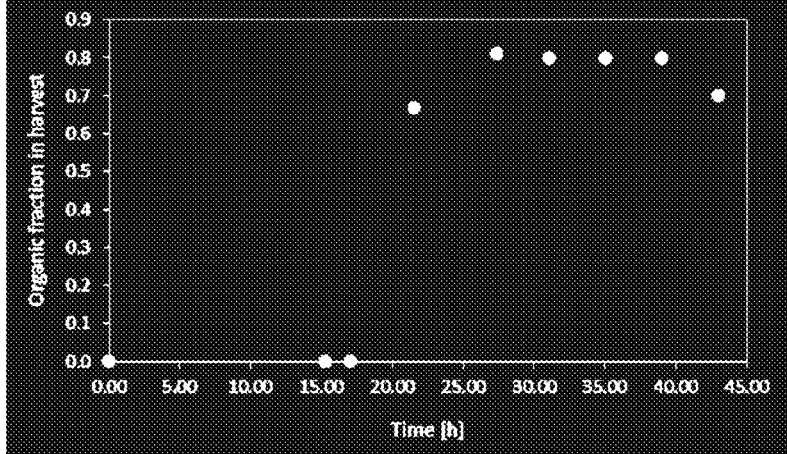
FIG. 26 shows concentration of an organic fraction of the harvest (recovered phase).

FIG. 26 shows the organic fraction of the harvest (recovered phase)

Figure 27:
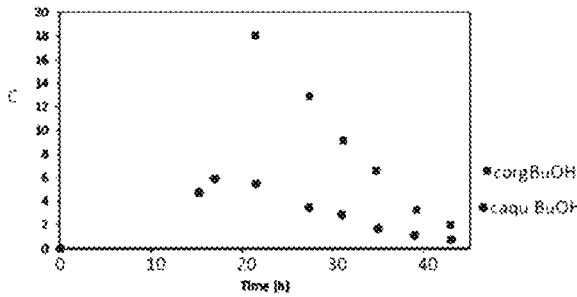
FIG. 27 shows a butanol concentration in the aqueous phase (caqu) and in the organic phase (corg).

FIG. 27 shows the butanol concentration in the aqueous phase (caqu) and in the organic phase (corg). The butanol concentration increased during the batch phase to approximately 6 g/L. With the start of the recovery phase addition, a lot of the butanol was extracted into the recovery phase. The productivity of the microorganism decreased after the batch phase which is why the butanol concentration is decreasing during the continuous phase.

Example 2: Recovery of an Aerobically Produced Hydrocarbon

A hydrocarbon (the sesquiterpene humulene) was fermentatively produced by a genetically modified *E. coli*, using castor oil as product recovery phase in an integrated bioreactor system (apparatus) as schematically shown in FIG. 1, having a volume of 100 L. Such *E. coli* and the use thereof in the fermentative production as such are generally known in the art. See also Semra Alemdar et al eng. Life Sci 2017, 17, 900-907 (https://onlinelibrary.wiley.com/doi/full/10.1002/elsc.201700043).

LB medium (Luria Bertani medium) was autoclaved and glucose was added sterile with a final concentration of 10 g/L. The preculture was inoculated with 1.2 mL cells from cryogenic frozen culture stocks in 500 mL LB medium in a flat bottom flaks with baffles. 5 flasks were prepared and the preculture was incubated for 8 h at 30° C. and 250 rpm.

Before the LB medium was filled into the 100 L integrated bioreactor system, the pH and DO (dissolved oxygen) probes were calibrated. Afterwards an empty sterilization of the reactor system was performed for 30 min at 125° C. and the LB medium was filled into the fermentation compartment of the reactor system. A full sterilization of the reactor was subsequently performed for the sterilization of the LB medium (121° C., 20 minutes). Only after full sterilization and cooling of the reactor, the batch sterile solutions were pumped into the reactor. The fermentation controllers: pressure, stirring, air flow, temperature, foam and pH should be started in the eZ-control unit (control system of the reactor) with indicated fermentation set points (Table 4). Afterwards, the DO calibration (2-point calibration) can be performed.

The fermentation compartment of the bioreactor system was supplied with aqueous fermentation broth, comprising substrate predominantly at carbon limiting conditions) and the *E. coli*. This supply was based on standard procedure, with the proviso that additionally product recovery phase (30 to 40 g/kg castor oil) was dispersed in the aqueous medium.

TABLE 5

| Parameter | Value | Unit |
|---|---|---|
| Initial set points of the batch phase | | |
| Vessel pressure | 0.3 | Barg |
| Air flow | 47 | L/min |
| | 1 | vvm (in the ferm. compart.) |

TABLE 5-continued

| Parameter | Value | Unit |
|---|---|---|
| Initial set points of the batch phase | | |
| DO (fed-batch) | >30 | % |
| Stirring | Batch: 700 | rpm |
| | Fed-batch: 400-700 | rpm |
| Anti-Foam controlled by sensor | on contact | — |
| | Cycle time: 3 | S |
| | Dead time: 15 | S |

During the batch phase the cells grew exponentially until the initial amount of glycerol is consumed. The oxygen saturation started to drop from 100% after about 1 hour. Just before the end of the batch, the DO decreased close to 0% shortly and increased abruptly to 100% at the end of the phase. At the end of the batch phase, the pH increased due to consumption of secondary metabolites, therefore pumping of acid was required. The foam was controlled by the foam sensor according to the defined cycle.

Figure 9:
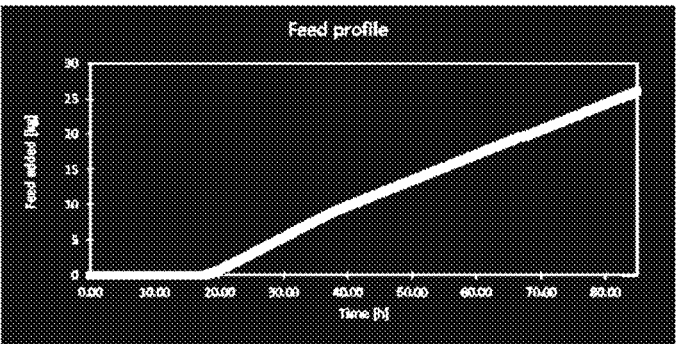
FIG. 9 shows total amount of aqueous substrate solution added during a continuous fermentation phase.

The fed-batch phase began when all substrate of the batch was consumed and oxygen saturation increased up to 100% starting with an exponential feed phase (see also FIG. 9 for details on accumulated feed addition throughout the fermentation). During this phase, the separation compartment also gradually became filled with fermentation broth. During this phase, the cells grew at an exponential rate but still under carbon limiting conditions. The next feed phase was at a constant rate, to avoid further oxygen limitations and to match a desired biomass concentration set point in the reactor. When the feed rate reached the desired set point during the exponential feed phase (initial 200 g/h), the software transited automatically to the constant feed phase regime and maintained the current feed set point (450 g/h). Both the fermentation and separation compartment were full of fermentation broth from the beginning of the fermentation. Therefore, the recirculation loop was open (maximum) since the beginning of the fermentation to ensure biomass recirculation, enough nutrients supply and to prevent oxygen limitation. The level control loop—which was control based on the height of broth in the separation compartment—was started after exponential feed. The height set point was defined as the current measured value which was expected between 700 and 800 mm. From that point onwards, the bleed rate (broth drawn from the recirculation loop) should match the feed rate, so that the level in the reactor was maintained.

The continuous addition of the product recovery phase, castor oil, to the fermentation compartment of the reactor was started at 37 hours after inoculation.

Product recovery phase, containing the humulene was formed as a top layer in the separation compartment; this was removed intermittently from the separation compartment, without using gas injection into the separation compartment. Flow conditions were laminar inside the separation compartment. The bottom layer (aqueous phase comprising *E coli*) was partly recycled and partly bled.

FIGS. 2-10 provide information about the flow rates and results of the experiment.

Figure 2:
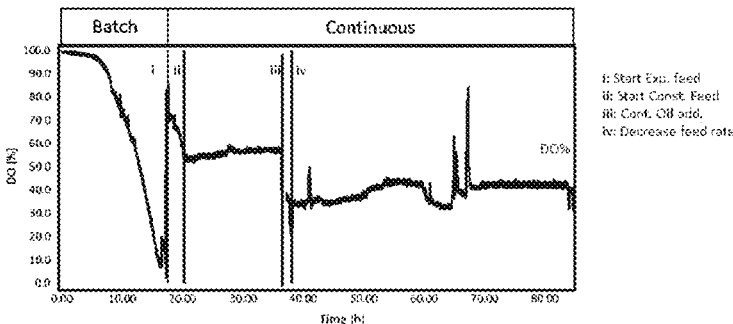
FIG. 2 shows a dissolved oxygen (DO) profile during fermentation, including indications of changes in process parameters corresponding to different feeding and operating phases.
Figure 3:
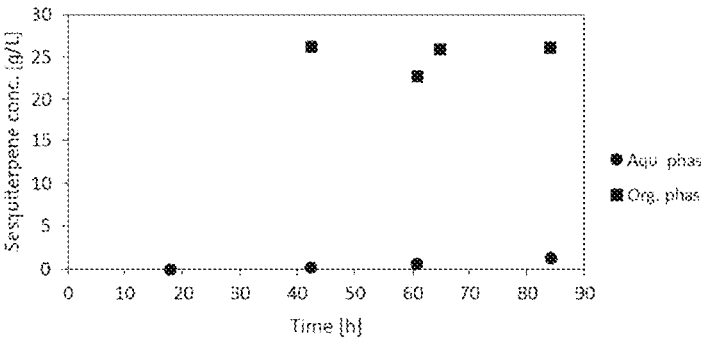
FIG. 3 shows a concentration of product in an aqueous phase and in an organic phase during fermentation, illustrating enrichment of the product in the organic phase.

FIG. 2 shows dissolved oxygen (DO) profile during the fermentation. The grey vertical lines show subsequent starts of changes in the process parameters. From left to right (second from the top to bottom in the legend:

Start Exp. Feed=start exponential feed phase
Start Const. Feed=constant feed phase
Cont. Oil add.=start of the continuous addition of castor oil, decrease feed rate FIG. 3 shows the product concentration in organic and aqueous phase. The product concentration is highest in the organic phase. So the transfer from the aqueous phase to the organic phase was successful and the organic phase was enriched with product compared to the aqueous phase.

The concentration of humulene in the aqueous phase increased only slightly during the fermentation while the concentration in the organic phase remained constant. A semi steady state was achieved during the fermentation, sufficient to keep the concentration of the humulene at a non-inhibiting level.

Figure 4:
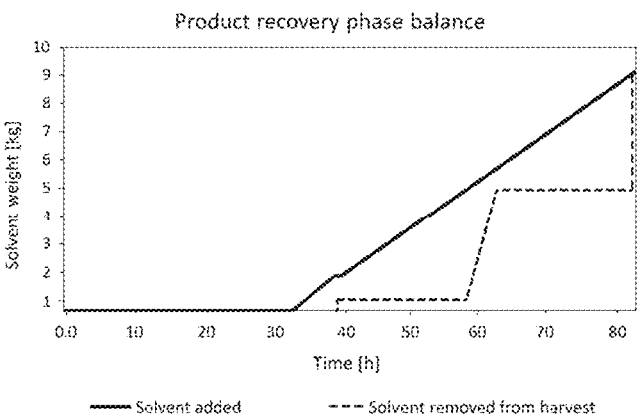
FIG. 4 shows an amount of product recovery phase added to a reaction section and the amount harvested from a separation section over time.

FIG. 4 shows the amount of product recovery phase (solvent for the product) added to the reaction section and recovered from the separation section (harvest). The partitioning coefficient depends on the concentration in both phases. The partitioning does not necessarily scale linear with the concentrations. That is why the aqueous product concentration can increase slightly while the organic concentration remains constant. The harvest of organic phase from the separation section occurred intermittently while the solvent addition was continuously.

Figure 5:
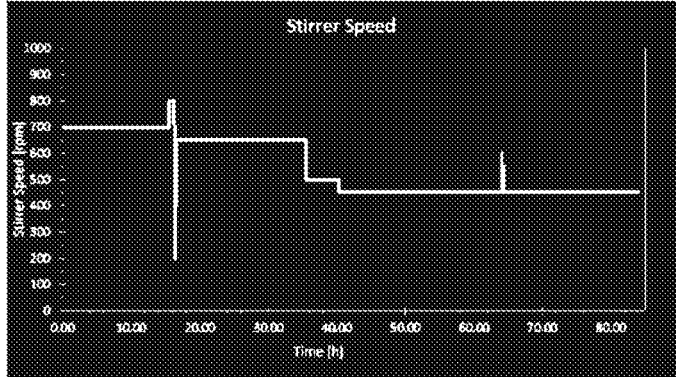
FIG. 5 shows a stirring speed during fermentation, demonstrating conditions suitable for maintaining turbulent flow and a desired droplet size range.

FIG. 5 shows the stirring speed during the fermentation. The stirring speed was suitable to maintain turbulent flow conditions in the fermentation reactor and D[3,2] at a value in the range of about 10 to about 100 μm.

Figure 6:
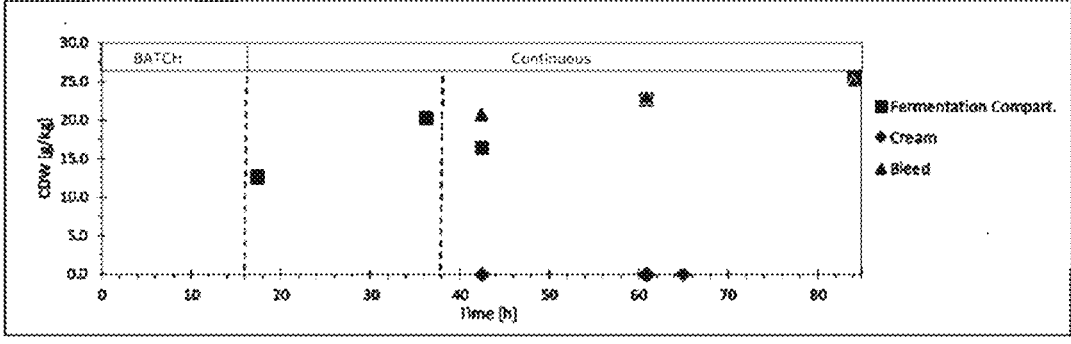
FIG. 6 shows a cell dry weight in a reaction medium and in an organic phase recovered from a separation section during fermentation.

FIG. 6 shows the cell dry weight (CDW) during the fermentation in the reaction medium inside fermentation compartment and in the organic phase formed by the castor oil plus product (cream, top layer in the separation compartment) from separation section. The cell biomass was mainly in the reaction section and bleed. The biomass was not found or in a very small concentration found in the cream in the separation section. So the harvested organic phase was considered to be free of cells which is beneficial for further DSP. Moreover, the cells were not lost with the harvest but recycled to the reaction section (fermentation compartment).

Figure 7:
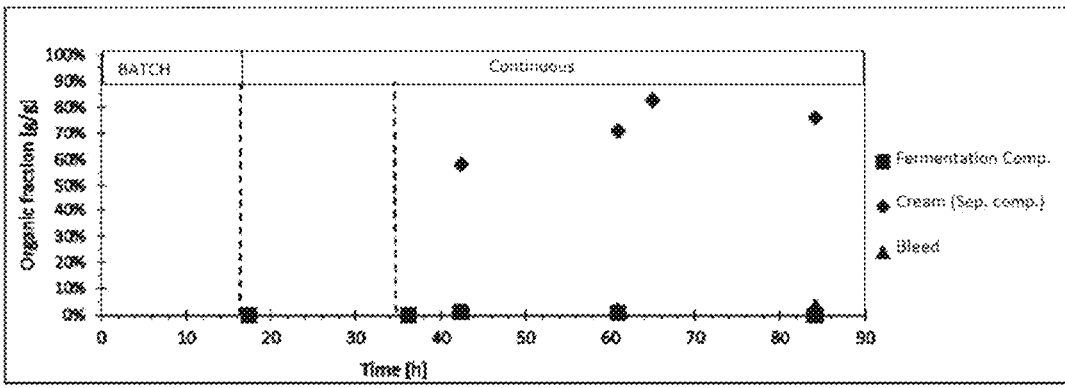
FIG. 7 shows a fraction of organic phase present in different compartments of the bioreactor system.

FIG. 7 shows the fraction of the organic phase in the different compartments (the content of organic phase in the reaction compartment was 1-4%, which was at a desired level).

Figure 8:
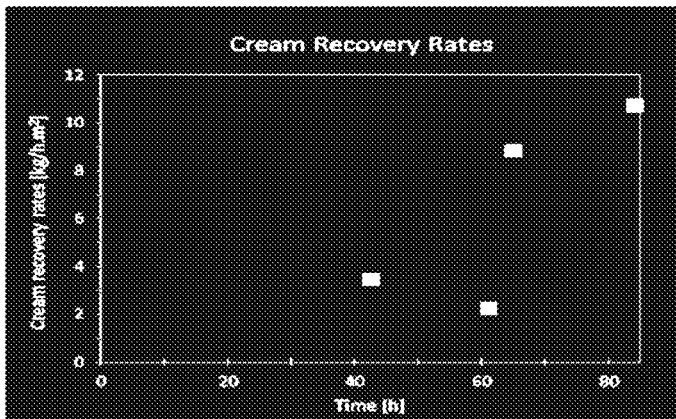
FIG. 8 shows a recovery rate expressed as a cream recovery rate from the separation section.

FIG. 8 shows the recovery rate expressed as cream recovery rate from the separation section.

FIG. 9 shows the total amount of aqueous solution of substrate added during the continuous phase.

Figure 10:
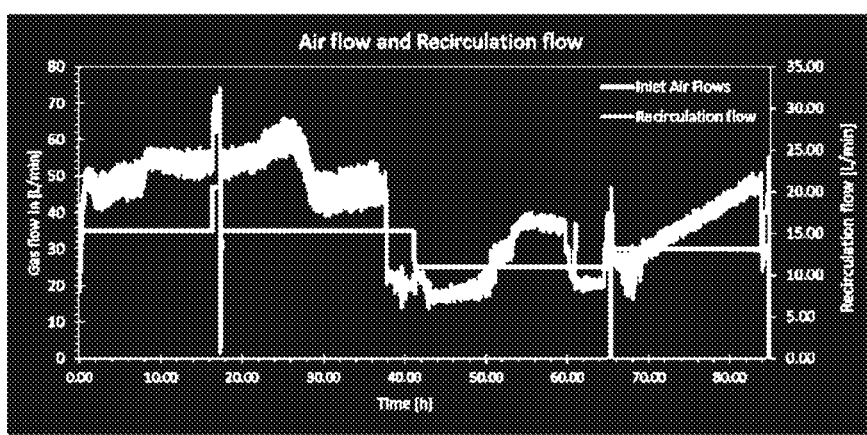
FIG. 10 shows an air-flow set point and a recirculation flow during fermentation.

FIG. 10 shows the air flow set point and recirculation flow during the fermentation.

Example 3: Determination of the Product Recovery Particle Size

Santalene was produced by a genetically modified E. coli using dodecane as product recovery phase under turbulent flow conditions in the fermentation compartment.

Figure 12:
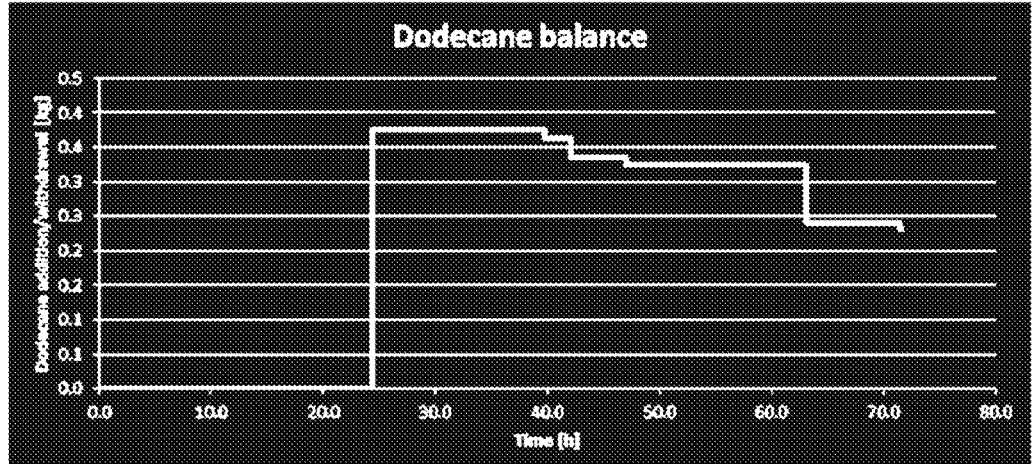
FIG. 12 shows a balance of a product recovery phase added to and removed from a bioreactor system over time.

The fermentation compartment was a CSTR (volume of 7 l). The pH and DO probe were calibrated before the fermentation. At the start sterile batch medium was pumped into the sterile fermentation compartment. The batch medium composition was as in Example 2. The batch medium had a volume of 3 L. Glycerol was the carbon source (substrate). The product recovery phase, dodecane, was added 24 h after inoculation of the reactor, after which it was intermittently withdrawn, see also FIG. 12 for the dodecane balance over time. The glycerol feed was started when the DO value reached >15% after a drop to almost 0%.

Droplet Size

This method is generally applicable to determine D[3,2] in a method according to the invention, in particular for liquid recovery phase.

During the fermentation, images of the product recovery droplets were recorded by a SOPAT probe (SOPAT Gmbh; https://SOPAT.de) which consisted of a probe that could be placed into the fermentation vessel coupled to a computer system. To provide sufficient lighting for the pictures a back lighting was applied. The image analysis software was capable of dealing with high oil fractions and the presence of cells in the fermentation broth.

Droplet measurements by SOPAT were conducted at the end of a fermentation run in a non-sterile way with no overpressure on the system. The SOPAT probe was put through the headplate into an open position of a push-valve. Both mirror and lens of the SOPAT were covered with a thin layer of Rain-X Rain repellent.

To clean the lens, the probe had to be removed from the reactor and placed back again. Cleaning of the probe was performed with 70% ethanol wipes and rinsed afterwards with MilliQ water.

For in situ image acquisition three hours online measurements were taken. Every 3 minutes, 30 pictures were acquired every five minutes, starting at 5 min and ending at 175 min. After the experiment, the accompanying particle detection software was used to measure the size of the droplets in the pictures provided by SOPAT Gmbh, see also Maaß, S., Rojahn, J., Hänsch, R., Kraume, M., (Computers & Chemical Engineering. 45. 27-37. 10.1016/j.compchemeng.2012.05.014). "A MATLAB® based image recognition algorithm has been implemented to automatically count and measure particles in multiphase systems.

A given image series is pre-filtered to minimize misleading information. The subsequent particle recognition consists of three steps: Pattern recognition by correlating the pre-filtered images with search patterns, pre-selection of plausible drops and the classification of these plausible drops by examining corresponding edges individually."

During a fermentation, air bubbles are present in the mixture interfering with the image analysis. These false positives were eliminated by setting a maximum particle size of 200 μm which was validated by manual removal of the air bubbles. The detected droplets were converted to size distributions and values for the Sauter mean diameter. The number of pictures was not sufficient to have more than 1000 droplets per data point as you statistically would have needed.

The Sauter mean diameter D[3,2] (a.k.a. $d_{32}$) is calculated with ($d_{32} = \Sigma d_i^3 / \Sigma d_i^2$).

Results of the droplet size measurement are shown in the following Table.

TABLE 6

| Results of the measurement of the droplet size | |
| --- | --- |
| average Particles/Folder | 2220 |
| total Particle number | 2220 (2220) |
| scale factor [μm/Pixel] | 1 |

| Single Output Values | | |
| --- | --- | --- |
| Parameter | mean | Meaning |
| dg [μm] | 31.35 | (Geometric Mean) |
| d1, 0 [μm] | 45.14 | (Arithmetic Mean) |

TABLE 6-continued

| Results of the measurement of the droplet size | | |
|---|---|---|
| d2, 0 [μm] | 54.86 | (Number-Surface Mean) |
| d2, 1 [μm] | 66.67 | (Length-Surface Mean) |
| d3, 2 [μm] | 74.06 | (Sauter Mean) |
| d4, 3 [μm] | 76.89 | (De Brouckere Mean) |

Relation of Droplet Size and Recovery Rate

Figure 11:
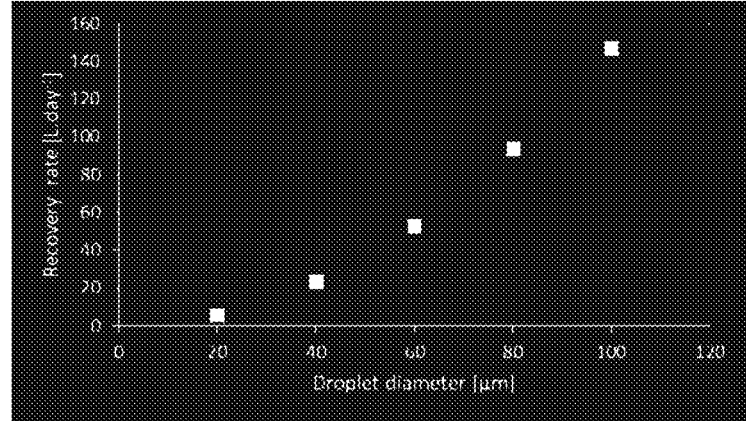
FIG. 11 illustrates a relationship between droplet size of a dispersed product recovery phase and recovery rate, including reference to droplet rise velocity.

The droplet size determines how fast the droplets can rise in the separation section and thus determine also the recovery rate. The rising velocity $v_c$ of the droplets can be calculated with Stokes law:

$$v_c = \frac{(\rho_{oil} - \rho_{water}) \cdot g \cdot d_d^2}{18 \cdot \mu}$$

with the droplet diameter $d_d$ and viscosity $\mu$ and density $\rho$, see also FIG. 11.

TABLE 7

| Assumptions for the theoretical recovery rate in a 100 L pilot system | | |
|---|---|---|
| Parameter | Value | Unit |
| Density dodecane | 750 | kg/m³ |
| Density water | 1000 | kg/m³ |
| Gravitational constant g | 9.81 | m/s² |
| Liquid viscosity water | 0.001 | Pa · s |
| Liquid viscosity dodecane | 0.001344 | Pa · s |
| Area separation | 0.025 | m² |
| Pressure, temp. | (1 bar, 298K) | |

Example 4: Production and Recovery of Humulene in a Bioreactor System, Comprising an Additional Fermentor Upstream of the Apparatus with Fermentor Compartment and Separator Compartment

The microorganism, product and solvent were as for Example 2: genetically modified *E. coli*, humulene, castor oil.

Figure 13:
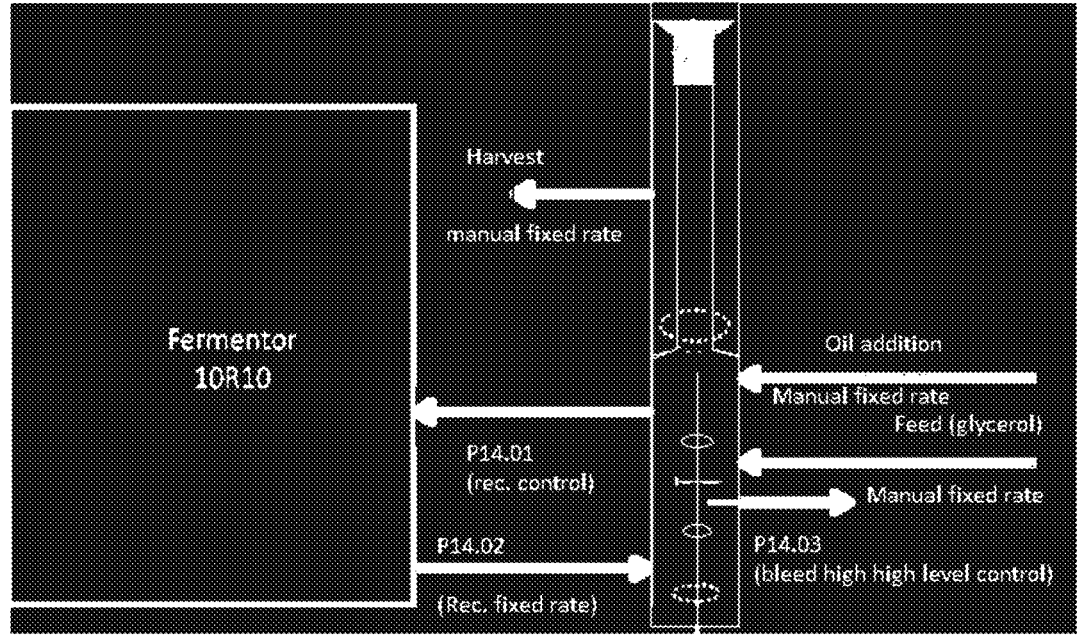
FIG. 13 is a schematic representation of an integrated reactor system connected to an upstream fermenter, allowing liquid exchange between reactors.

The setup of the experiment was as followed: An apparatus according to the invention (having a bottom fermentation compartment and a top separation compartment, in connection via a centrally positioned riser surrounded by a downcomer and an internal recycle (not shown in graph) was connected to a big 1 m³ fermenter (called 10R10) so that liquid could be exchanged between the big fermenter and the reaction section of the integrated reactor system, as schematically shown in FIG. 13. The experiment was divided into two stages—batch and continuous stage.

The fermentation started with the batch phase in the 1 m³ reactor. The operational conditions are shown in the following Table.

TABLE 8

| Operational conditions in the 1 m³ fermenter | | |
|---|---|---|
| Parameter | Value | Unit |
| Vessel pressure | 0.4 | barg |
| Air flow | 1 | vvm |
| DO (constant feed) | >30 | % |

TABLE 8-continued

| Operational conditions in the 1 m³ fermenter | | |
|---|---|---|
| Parameter | Value | Unit |
| Stirring | DO Cascade (stirring only) Min 100 | rpm |
| Antifoam | Yes: on contact | |

During the batch phase the cells grew exponentially until the initial amount of glycerol was consumed. The oxygen saturation began to drop from 100% after about 1 hour. Just before the end of the batch, the DO decreased close to 0% shortly and then increased abruptly to 100%. This happened about 12 to 15 hours after the inoculation. The continuous phase began when all substrate was consumed and oxygen saturation increased up to 100%. The feed addition was activated and the start constant feed rate was 0.93 kg/h. The cascade DO control was set to min. 24% and controlled with the stirrer speed. There was no overpressure or feed rate or air flow rate adjustment.

After the end of the batch phase, the integrated reactor/separator was filled with broth of the 1 m³ reactor. The feed addition (350 g/h) and the addition of product recovery phase (oil/solvent addition) at a fixed rate for 0.47 kg/h for 42 hours was started (see also FIG. 19). The operational conditions for the integrated reactor is shown in the following Table.

TABLE 9

| Operational conditions of the integrated reactor (100 L) during the continuous phase | | |
|---|---|---|
| Parameter | Value | Unit |
| Vessel pressure | 0.5 | barg |
| Air flow (bottom) | (MAX) 25 | L/min |
| | 0.5 | vvm (in the ferm. compart.) |
| DO | >30 | % |
| Stirring | Fed-batch: 400-700 | rpm |
| Anti-Foam cycle | Foam: on contact | Yes |
| Always controlled by sensor | Cycle time: 3 | s |
| | Dead time: 15 | s |

The recirculation loop between fermentation compartment and separation compartment was opened to the maximum once the integrated reactor was filled with broth.

The results of the integrated reactor are shown in FIGS. 14-20.

Figure 14:
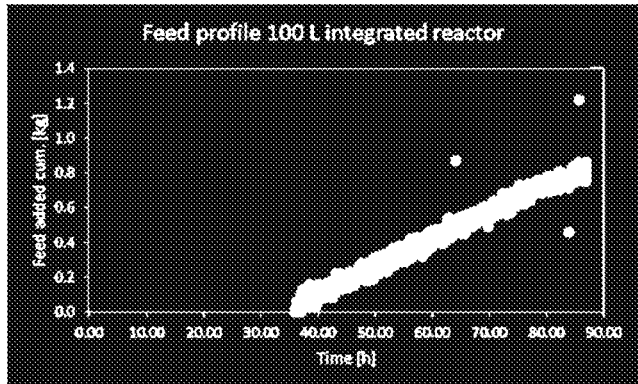
FIG. 14 shows feed added to the integrated reactor during the continuous phase.
Figure 15:
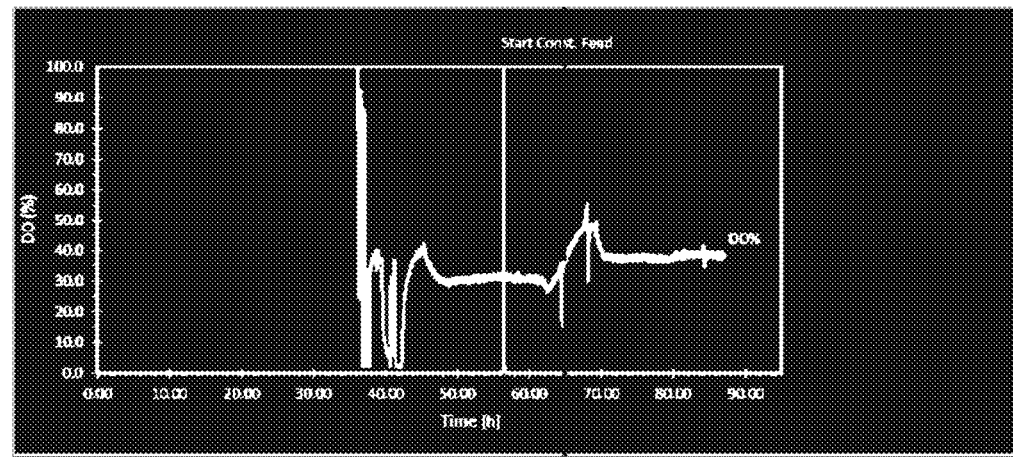
FIG. 15 shows a DO profile in the fermentation compartment of the integrated apparatus.
Figure 16:
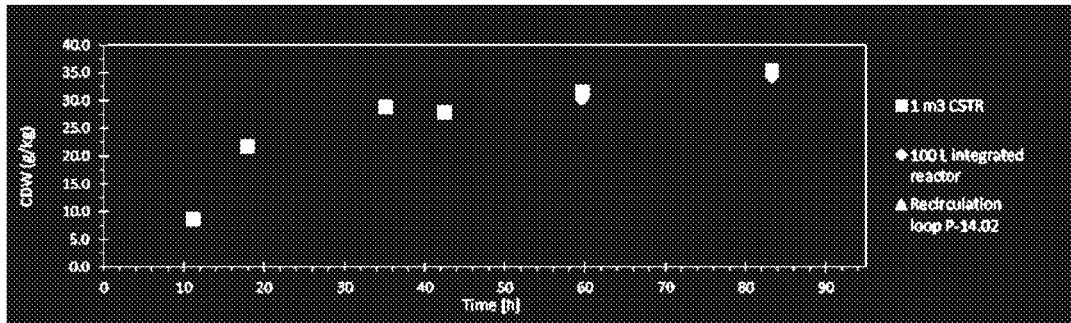
FIG. 16 shows a development of the cell dry weight (CDW) in the 1 m³ fermenter and the integrated reactor.

FIG. 14 shows feed added to the integrated reactor during the continuous phase FIG. 15 shows the DO profile in the fermentation compartment of the integrated apparatus FIG. 16 shows the development of the cell dry weight (CDW) in the 1 m³ fermenter and the integrated reactor. The CDW concentration was the same in the 1 m³ fermenter and the integrated reactor system (reaction system). There was no concentration gradient and there was a homogeneous exchange of liquid between the two reactors.

Figure 17:
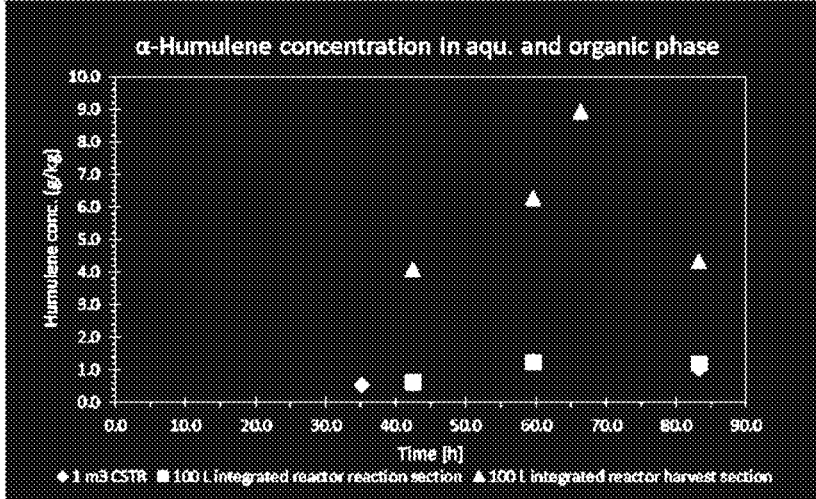
FIG. 17 shows a product concentration in the aqueous phase (1 m³ fermenter, reaction section—of the integrated reactor system) and the organic phase (in the separation section, i.e. harvest section, of the integrated reactor system) during the continuous phase.

FIG. 17 shows the product concentration in the aqueous phase (1 m³ fermenter, reaction section—of the integrated reactor system) and the organic phase (in the separation section, i.e. harvest section, of the integrated reactor system) during the continuous phase. The product was enriched in the organic phase and successfully transported to the separation section of the integrated reactor system.

Figure 18:
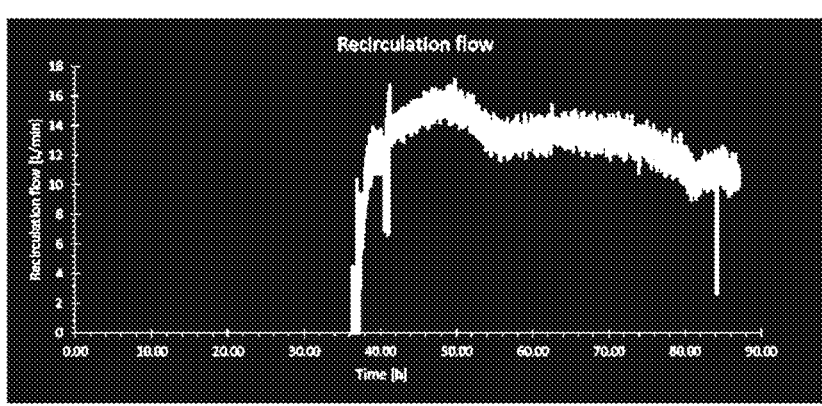
FIG. 18 shows a recirculation flow from the separation compartment to the reaction compartment of the 100 L apparatus during the continuous phase.

FIG. 18 shows the recirculation flow from the separation compartment to the reaction compartment of the 100 L apparatus during the continuous phase.

Figure 19:
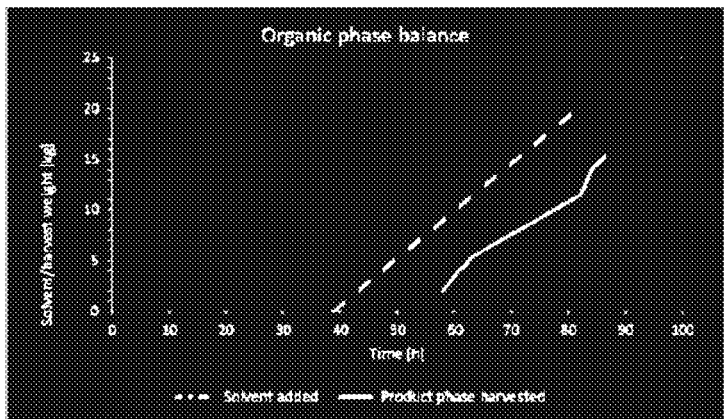
FIG. 19 shows an amount of organic phase (castor oil, 'solvent') added to and organic phase harvested from the integrated reactor system during the continuous phase.

FIG. 19 shows the amount of organic phase (castor oil, 'solvent') added to and organic phase harvested from the integrated reactor system during the continuous phase. After the filling of the integrated reactor/separator and dosing of the solvent, the apparatus was able to separate the phases quickly without a long lag phase. The total amount of solvent was more than twice as much as compared to Example 2. So the fermentation capacity was increased by connecting the integrated reactor system to the 1 m$^3$ fermenter while the area for phase separation remained the same. It was proven that the given size of the separation section can cope with bigger amounts of fermentation capacity.

Example 5: Soybean Oil as Recovery Phase

This experiment was performed similarly as Example 3 except that the product recovery phase was only added to the 100 L integrated reactor/separator apparatus. At the end of the fermentation, high solvent addition rates and the respective recovery rates were investigated. The solvent for this test was soybean oil. This lead to the higher recovery rate measured: 4.4 L/h or 172.7 L/m2/h.

Example 6: Effect of Recovery Phase

An experiment was performed similar to Example 2 but with an alkane (dodecane) as solvent, instead of a triglyceride oil (castor oil). Using dodecane as recovery phase was effective but resulted in lower recovery rates, see FIGS. 28 and 29.

Figure 28:
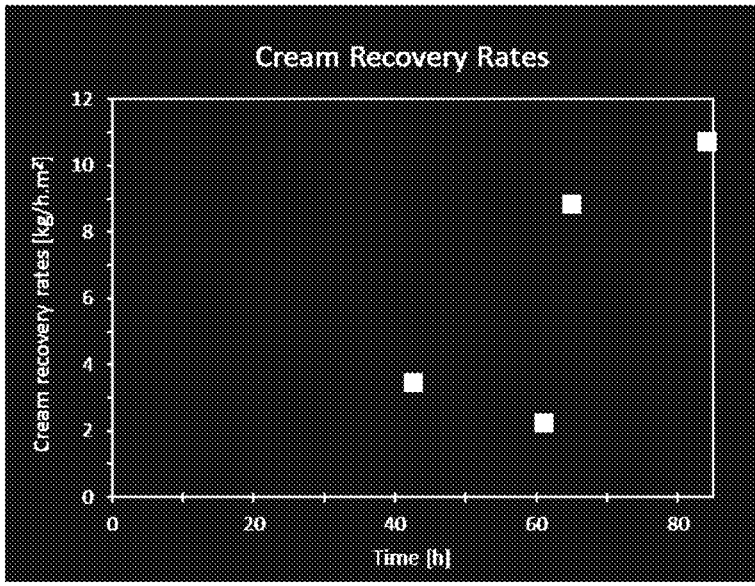
FIGS. 28-29 show recovery rates obtained using different product recovery phases.
Figure 29:
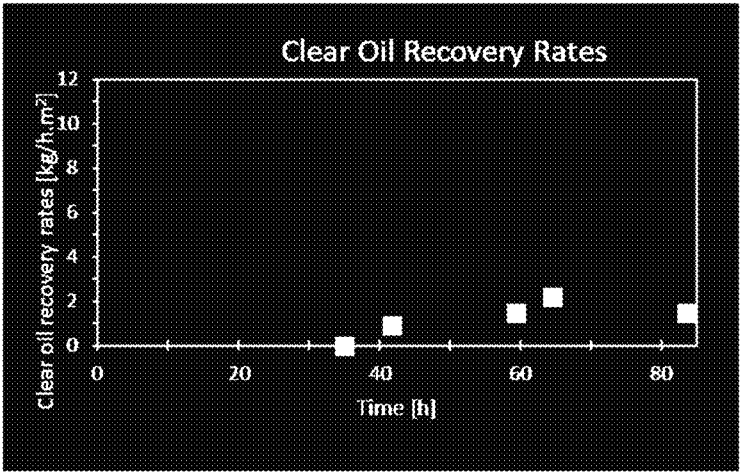

FIG. 28 shows a high recovery rate when castor oil was used. The product containing phase was a cream with very high organic fraction [0.77-0.83]. FIG. 29 shows that the recovery rate with dodecane was lower. The net rate difference (kg/h) is almost a factor of 5. The droplets distribution of dodecane is significantly smaller, among others due to surface tension and viscosity difference compared to castor oil. The product containing (dodecane) phase was a cream also containing fractions of clear oil with a fraction of organics of 0.6-0.72.

Example 7 butanol Production with Addition of oleyl alcohol as Recovery Phase During the Batch Stage The setup of the experiment was similar to Example 4 except for the initial batch medium and solvent addition. The initial batch medium was 30 L and 29 kg of liquid recovery phase (solvent; techn. oleyl alcohol) was added during the batch stage.

Figure 30:
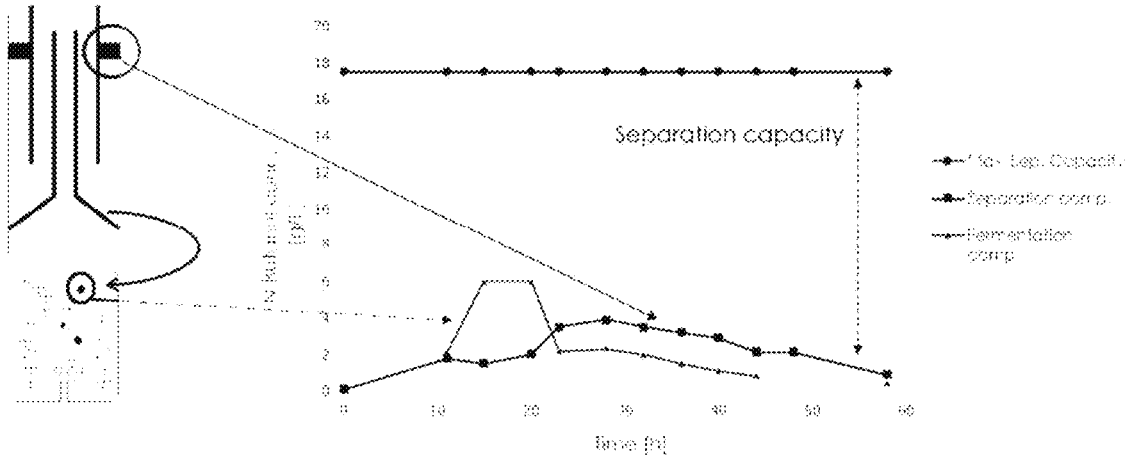
FIG. 30 FIG. 30 shows a butanol concentration in the organic phase in the fermentation compartment and in the separation compartment.

FIG. 30 shows the butanol concentration in the organic phase in the fermentation compartment and in the separation compartment. The maximum concentration of butanol possible in this set up at steady state was about 18 g/L in the organic phase.

Theoretical steady states for butanol production in a 100 L integrated reactor system according to the invention, as schematically shown in FIG. 1:

TABLE 10

| Assumptions made to estimate steady state points for a theoretical butanol production via fermentation. $N_X$ - biomass, $q_P$ - specific production rate, P - product. | |
|---|---|
| Assumptions | Value |
| Solvent partitioning m | 4 |
| Solvent partitioning m | 10 |
| Solvent partitioning m | 15 |
| Solvent addition [kg/h] | 6.048 |
| $q_P$ [$kg_P/kg_X/h$] | 0.41 |
| $N_X$ [kg] | 2.5 |
| $V_{ferm}$ [L] | 100 |
| $c_{inhibition}$ [g/L] | 20 |

Figure 31:
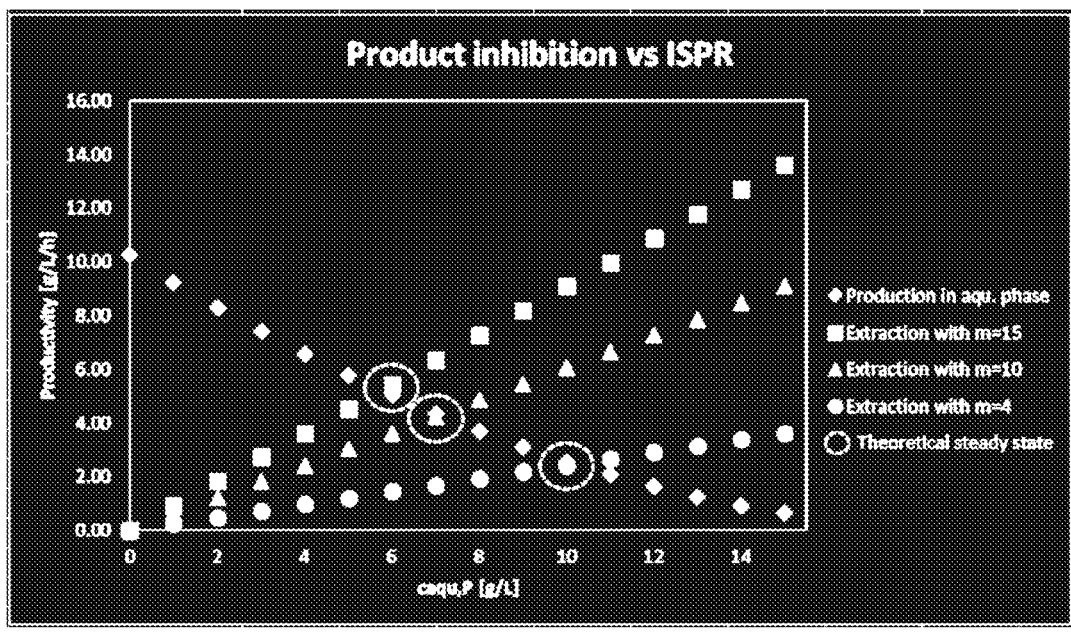
FIG. 31 shows an effect of product inhibition on the microorganism's expected productivity and thus the effect of ISPR on the productivity.

FIG. 31 shows the effect of product inhibition on the microorganism's expected productivity and thus the effect of ISPR on the productivity. For the three different solvents shown (each with their own butanol partitioning (m=4, 10, 15), three different steady states can be calculated, indicated by the dotted circles. P—product, aqu—aqueous, m—partitioning of product in solvent and aqueous phase, in this example.

Example 8: Recovery of vanillic acid

Vanillin was catalytically converted into vanillic acid by *S. cerevisiae* CEN.PK.113-7D. Technical oleyl alcohol was used as the primary product recovery phase (solvent) during cultivation and it was coloured with 75 mg/$kg_{solvent}$ Oil Red O to visualize the solvent. The integrated bioreactor was prepared similar to example 1, except with fermentation air as aeration medium and the batch medium was SMD2 medium.

A preculture was performed in 5 shake flasks with baffles with 100 mL YPD medium (10 g/L Bacto-yeast extract, 20 g/L Bacto-peptone, 20 g/L glucose; e.g. BD, Difco™& BBL™manual, 2$^{nd}$ edition https://legacy.bd.com/europe/regulatory/Assets/IFU/Difco_BBL/242820.pdf) each. Each flask was inoculated with 1.8 mL frozen stock culture and incubated at 30° C. at 175 rpm for 16 h. 115 mL of the preculture was transferred to the integrated bioreactor. The integrated bioreactor was filled with 70 kg of SMD2 medium (Tables 11-13).

TABLE 11

| Batch medium composition | |
|---|---|
| Batch medium SMD2 | Final concentration |
| $(NH_4)_2SO_4$ | 5 g/L |
| $KH_2PO_4$ | 3 g/L |
| $MgSO_4 \cdot 7H_2O$ | 0.5 g/L |
| Bacterial Yeast Extract | 5 g/L |
| Sterile additions | |
| Glucose monohydrate | 30 g/L |
| Trace elements (1000x stock) | 1 mL/L |
| Vitamin solution (100x stock) | 10 mL/L |

TABLE 12

| Composition of the trace element solution which was adjusted to pH 6.7 with 5M NaOH. The solution was sterilized at 110° C. for 20 min and stored in the fridge wrapped in aluminium foil. | |
|---|---|
| Trace element solution | Concentration |
| $C_6H_6FeO_7$ (Fe(III)citrate) | 100 g/L |
| $CoCl_2 \cdot 6 H_2O$ | 4 g/L |

TABLE 12-continued

Composition of the trace element solution which was adjusted to
pH 6.7 with 5M NaOH. The solution was sterilized at 110°
C. for 20 min and stored in the fridge wrapped in aluminium foil.

| Trace element solution | Concentration |
| --- | --- |
| $MnCl_2 \cdot 4\ H_2O$ | 23.5 g/L |
| $CuCl_2 \cdot 2\ H_2O$ | 1.97 g/L |
| $H_3BO_3$ | 5 g/L |
| $Na_2MoO_4 \cdot 2\ H_2O$ | 4 g/L |
| $Zn(CHCOO)_2 \cdot 2\ H_2O$ | 16 g/L |
| EDTA | 8.4 g/L |

TABLE 13

Composition of the vitamin solution which was filter sterilized.

| Vitamin solution | Concentration |
| --- | --- |
| D-Biotin | 5 g/kg |
| Ca D(+) pantothenate | 100 g/kg |
| Nicotinic acid | 100 g/kg |
| Myo-inositol | 25 g/kg |
| Thiamine chloride | 100 g/kg |
| Pyridoxol hydrochloride | 100 g/kg |
| p-Aminobenzoic acid (paba) | 20 g/kg |
| Riboflavin | 50 g/kg |

TABLE 14

Composition of the feed medium

| Feed medium | Final concentration |
| --- | --- |
| Glucose monohydrate | 120 g/L |
| Yeast extract | 5 /L |

The cultivation in the bioreactor was performed in 3 stages. The first stage was a 16 h batch fermentation during which no solvent, nor feed, nor vanillin solution was added. The second stage (16 h to 43 h) was started with the feed addition (composition in Table 14) at 500 g/h, a solvent addition at rate of 0.34 kg/h and vanillin solution (10 g/L) addition at 0.23 kg/h. The third stage began after 43 h when the vanillin solution was added at 0.7 kg/h, while solvent addition and feed addition remained the same as in the second stage.

Samples of the fermentation broth (reaction section, bottom of reactor) and organic phase (separation section, top of reactor) were taken approximately every 2 h during the day and 3 samples during the night, starting at 16 h (directly after the end of the batch, stage 1).

The organic phase (including product recovery phase and product) were withdrawn with the start of stage 2 until the end of the fermentation. The pump was set to a fixed rate so that all separated organic phase would be harvested. The organic phase recovery rate was on average 0.1 kg/h during stage 2 and 0.18 kg/h during stage 3.

Main cultivation parameters can be found in Table 15. The pH was controlled with 25 (v/v) % $NH_4OH$ solution. The pH control was activated when the pH dropped below 4.5 and sufficient $NH_4OH$ solution was added to maintain the pH at 4.5.

TABLE 15

Cultivation parameters during batch, set point 1 and set point 2

| Parameter | Value |
| --- | --- |
| Temperature | 30° C. |
| Vessel pressure | 0.1 barg |
| Liquid working volume | ~70 L |
| Air flow | 30 L/min |
| pH | 6.3 to 4.5 |
| pH control | 25 (v/v)% $NH_4OH$ |
| Stirring | Batch (stage 1): 300 rpm |
| | Stage 2 and 3: 300-600 rpm |
| | (controlled to DO cascade 30%) |
| Antifoam control | Foam: on contact |
| Solvent | Oleyl alcohol |

Figure 32:
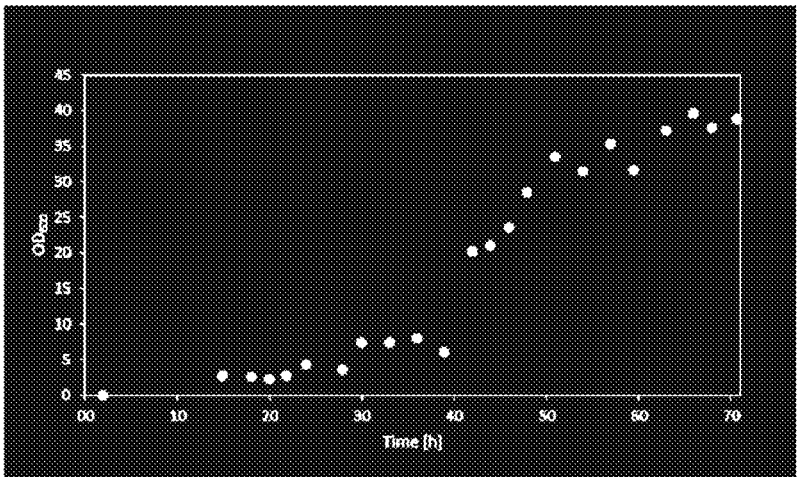
FIG. 32 shows microorganism growth in a method wherein vanillic acid is produced
Figure 33:
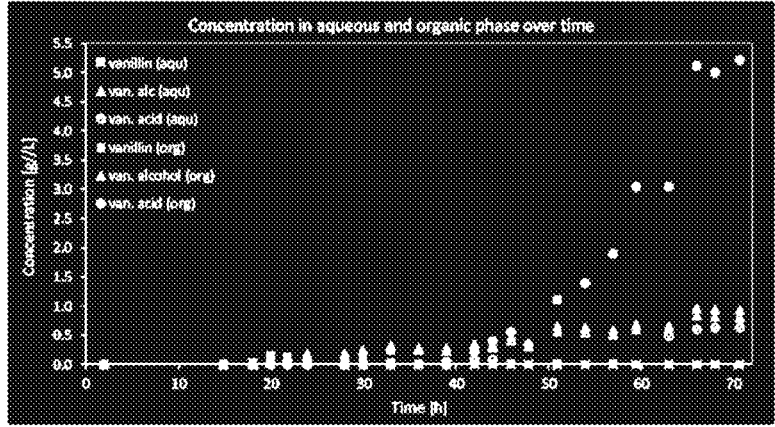
FIG. 33 shows concentration development in an organic phase and in an aqueous phase for several components in a method wherein vanillic acid is produced

Vanillin, vanillic acid and vanillic alcohol are potential inhibitors to microorganisms [Converti et al. Brazilian Journal of Microbiology (2010) 41: 519-530]. This is why the concentration of all of these components should be maintained at lower inhibiting concentrations in order to keep fermentation rates fast. Aqueous vanillin can already be toxic for microorganisms at a concentration of 0.5 g/L [Hansen et al Applied and Environmental Microbiology (May 2009), p2765-2774]. FIG. 33 shows that the aqueous vanillin concentration was below 0.5 g/L during the whole fermentation, while vanillic acid and vanillic alcohol were enriched in the organic phase (vanillin: square dark & square light, vanillic acid (van. acid): circle filled & circle pattern and vanillic alcohol (van. Alcohol: triangle filled & triangle pattern) in the organic and aqueous phase. The growth was not inhibited by the compounds present at the measured concentrations (FIG. 32). By harvesting continuously, the organic concentration of oleyl alcohol was maintained below 4%. This lower overall oil content (due to removal of oil in time) minimized the influence of the dispersed phase on the microorganism morphology. In this experiment, vanillic alcohol was formed as by-product.

Figure 34:
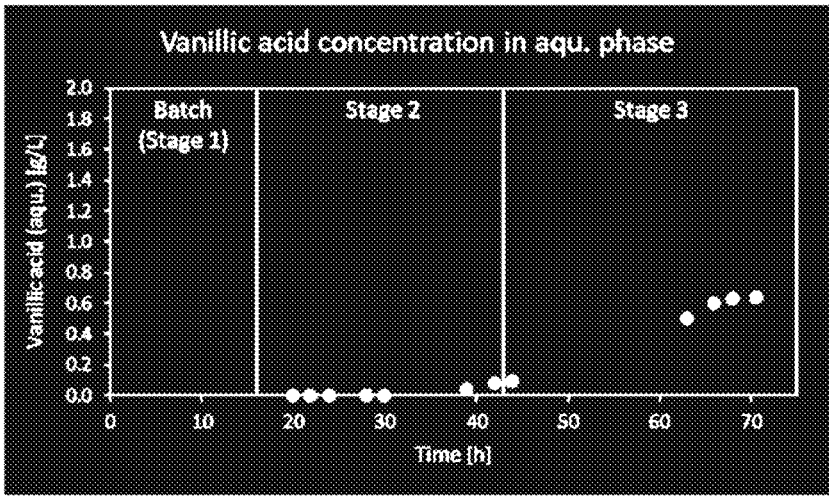
FIG. 34 shows vanillic acid concentration in an aqueous phase at different stages in a method wherein vanillic acid is produced.

The product of interest is vanillic acid. Vanillic acid was formed by S. cerevisiae and accumulated in the broth until the steady state was reached (FIG. 34 showing the vanillic acid concentration in the fermentation broth; the vanillic acid concentration in aqueous phase was analysed for stage 2 and the end of stage 3.4). At the end of stage 2 (set point 1, 43 h), the yeast began to convert vanillin to vanillic acid with a productivity of 0.009 g/L/h which increased to 0.026 g/L/h when the vanillin addition to the fermenter was increased. The steady state concentration of vanillic acid in the aqueous fermentation broth was approximately 0.63 g/L.

Figure 35:
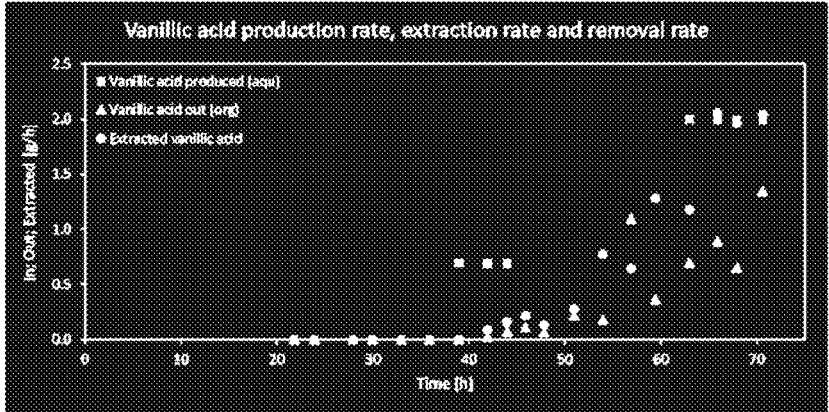
FIG. 35 shows a vanillic acid production rate, extraction rate and removal rate.

FIG. 35 shows the vanillic acid production rate (square), extraction rate (circle) and separation rate (triangle) over time. As can be seen in FIG. 35, the extraction rate equalled the production rate when all organic phase and aqueous phase concentrations remained constant (or steady state) which is from ~65 hours onwards. The net organic phase extraction and production rate were around 0.002 kg/h vanillic acid.

The overall product removal rate from the reactor at the end of the fermentation was >70% of the net production of product at that time. When taking into account limitation in analyses methods, hold-up changes during time due to system kinetics and mass balance gaps, the overall product removal rate is close to the net product rate, especially between 40-50 h. If desired, an increase in overall organic phase recovery can be achieved if emulsion stability is controlled more tightly. Stability, possibly increased by the 0.6 kg antifoam 98/007K (Basildon Chemicals) dosed, can be optimized further.

The production rate was maintained high and the inhibition low by extracting the inhibiting compounds into the organic phase. The production rate was successfully increased during the third stage (set point 2, after 43 h).

Example 9: Back-Extraction of vanillic acid

Vanillic acid obtained from catalytical conversion within Example 8 was extracted from the product recovery phase (oleyl alcohol) into an auxiliary solvent (70 (v/v) % ethanol in water). The organic phase withdrawn from the separation section in the top of reactor, consisting mostly of oleyl alcohol, vanillic acid and vanillic alcohol, was centrifuged at 4000 rpm for 20 min to remove possible solid residuals. Afterwards, the organic phase was divided into 3 sets of duplicates, each with 3.5 mL organic phase. The sample sets were overlaid with 70% ethanol solution in the following amounts—2 mL (sample number 1, 2), 3 mL (sample number 3, 4) and 6 mL (sample number 5, 6)—and mixed at room temperature for 1 h. Oleyl alcohol and 70% ethanol formed two phases before and after mixing. In order to ensure clean liquid/liquid phase separation, the samples were centrifuged at 4000 rpm for 20 min after the mixing step. The samples were analysed according to their vanillic acid content in oleyl alcohol.

Figure 36:
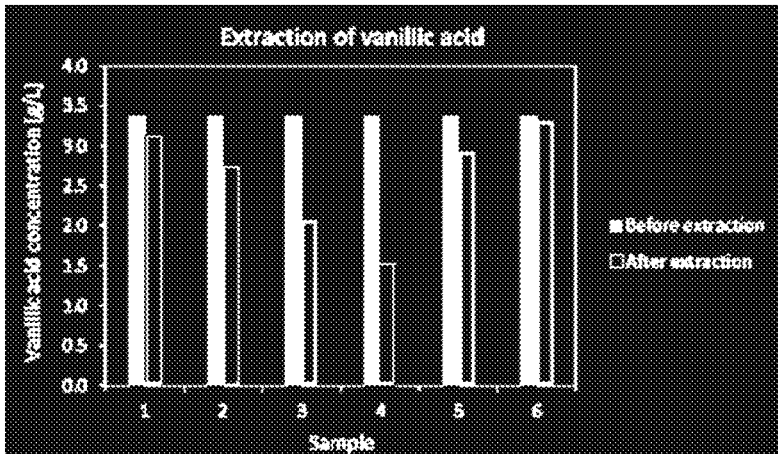
FIG. 36 shows vanilla concentrations before and after extraction in a back-extraction process.

FIG. 36 shows the successful back-extraction of vanillic acid from oleyl alcohol into 70% ethanol (auxiliary solvent). 70% ethanol has a lower boiling point than oleyl alcohol, which facilitates the downstream processing of the product towards the desired quality by solvent evaporation or (vacuum) distillation. The separation of vanillic acid and ethanol is less energy-intensive due to the overall stream size reduction and heat of evaporation of ethanol, which is noticeable lower then e.g. water. A remark here is that ethanol cannot be used directly in the fermentor as it is highly miscible with aqueous solutions. Therefore, oleyl alcohol was chosen as primary solvent for vanillic acid extraction from fermentation broth. Oleyl alcohol is not toxic towards the microorganism, while maintaining adequate aqueous product concentration and phase separation properties.

Additionally, the back-extraction experiment confirms the benefit of enriching the product of interest in the auxiliary solvent (Table 16). Vanillic acid was enriched in ethanol compared to vanillic alcohol. Continuous extraction of vanillic acid in a reactor according to the invention (such as schematically shown in FIG. 1) by oleyl alcohol and back-extraction to low boiling solvent enabling further efficient downstream processing for product recovery.

TABLE 16

Concentration of vanillic acid and vanillic alcohol
before and after concentration demonstrating
enrichment of vanillic acid in 70% ethanol

| Sample | Vanillic acid in oleyl alcohol [g/L] | Vanillic alcohol in oleyl alcohol [g/L] | Vanillic acid in ethanol [g/L] | Vanillic alcohol in ethanol [g/L] |
|---|---|---|---|---|
| 1 | 1.15 | 0.25 | 3.62 | 0.82 |
| 2 | 1.31 | 0.30 | 3.59 | 0.78 |
| 3 | 1.17 | 0.30 | 2.42 | 0.50 |
| 4 | 1.39 | 0.30 | 2.13 | 0.48 |
| 5 | 0.55 | 0.19 | 1.60 | 0.32 |
| 6 | 0.47 | 0.17 | 1.55 | 0.31 |
| Before extraction | 3.37 | 0.75 | — | — |

46

Additionally, phase separation was tested for two different phase equilibria. Oleyl alcohol, including vanillic acid, was used as primary solvent (product recovery phase) in both experiments and either (i) 70% ethanol in water (aqueous ethanol) or (ii) hexylcinnamaldehyde were used as back-extraction solvent. 1.5 mL oleyl alcohol and 1.5 mL hexylcinnamaldehyde were mixed; 3.5 mL oleyl alcohol were mixed with 3 mL aqueous ethanol. The samples with hexylcinnamaldehyde were stored in the fridge overnight to identify the effect of temperature on phase separation. Two distinct phase equilibria were observed at the different temperatures. (i) was a liquid-liquid system of phases of aqueous ethanol and oleyl alcohol at room temperature. (ii) was a liquid-solid system of liquid oleyl alcohol and solid phase containing vanillic acid after cooling (6° C.). (i) and (ii) showed that a wide range of temperature is possible for phase separation strategies which can be used for the back-extraction of vanillic acid.

The invention claimed is:

1. A method for recovering a biocatalytically produced organic substance from a reaction mixture, comprising
providing a reaction mixture, wherein the substance is produced using a biocatalyst, which reaction mixture comprises an aqueous phase, in which the biocatalyst is dispersed or dissolved, which aqueous phase comprises a substrate for the biocatalyst, and wherein further droplets or bubbles of a fluid product recovery phase are dispersed in the continuous aqueous phase, into which droplets or bubbles produced substance migrates and wherein the product recovery phase has a lower density than the aqueous phase; and
separating the product recovery phase comprising the produced substance from the aqueous phase and the biocatalyst;
wherein the production of the organic substance and the separation of the product recovery phase are carried out in an apparatus comprising a reaction section, containing the reaction mixture wherein the substance is produced, and a separation section wherein the product recovery phase comprising the produced substance is separated from the aqueous phase,
wherein the method comprises a simultaneous production and separation stage,
wherein at least during said simultaneous stage,
substrate and/or product recovery phase is fed into the reaction section continuously or intermittently,
flow conditions in the reaction section are turbulent flow conditions,
reaction mixture—of which mixture the product recovery phase comprises the produced substance—is fed continuously or intermittently from the reaction section into the separation section, which fed reaction mixture enters said separation section under essentially laminar flow conditions, in which separation section the product recovery phase is separated from the aqueous phase, under essentially laminar flow conditions or intermittently alternating between laminar flow conditions and no-flow conditions, wherein the reaction mixture is separated into an upper layer comprising the product recovery phase enriched with produced substance and a lower layer comprising the aqueous phase, and
fluid product recovery phase, comprising the biocatalytically produced substance, is recovered continuously or intermittently from the separation section of the apparatus.

2. The method according to claim 1, wherein the migration rate, the absorption rate of the produced substance into the product recovery phase in the reaction section is at least during said simultaneous production and separation stage maintained at about the same rate as the rate at which produced substance (as part of the separated product recovery phase) is separated from the aqueous phase in the separation section and/or wherein the migration rate or absorption rate of the produced substance into the product recovery phase in the reaction section is maintained at about the same rate as the rate at which the substance is produced.

3. The method according to claim 1 or 2, wherein the Sauter mean diameter (D[3,2]), of the droplets or bubbles of the dispersed product recovery phase in the reaction section is maintained within the range of about 10 to about 250 μm.

4. The method according to claim 3, wherein the Sauter mean diameter (D[3,2]) of the droplets or bubbles of the dispersed product recovery phase in the reaction section is maintained within the range of about 150 to about 250 μm.

5. The method according to claim 1, wherein at least during said simultaneous production and separation stage the substrate and the product recovery phase are fed into the reaction section at a rate at which the production rate of the substance and the migration rate of the produced substance into the product recovery phase are about the same.

6. The method according to claim 1, wherein the concentration of the produced substance in the aqueous phase is maintained at a value at which the biocatalyst activity is essentially non-inhibited by the presence of the organic substance, at least during the simultaneous stage and/or wherein the concentration of biocatalyst-inhibiting contaminants originating from the substrate is maintained at a value at which the biocatalyst activity is essentially non-inhibited by the presence of the organic substance, at least during the simultaneous stage.

7. The method according to claim 1, wherein the product recovery phase is a liquid phase, preferably an organic liquid, for which the produced substance has a higher affinity than for the aqueous phase and which liquid phase is fed into the reaction section at least during the simultaneous stage, which product recovery phase is a phase for which the produced substance has a partitioning coefficient (i.e. the ratio of the equilibrium concentration of the produced substance in the product recovery phase to the equilibrium concentration of the produced substance in the aqueous phase) of at least 3.

8. The method according to claim 1, wherein at least during the simultaneous stage a gas is fed in a lower part of the reaction section, which gas may be a product recovery phase, and which gas generates or contributes to an upwards motion of the reaction mixture, whereby reaction mixture flows into a riser situated between the reaction section and the separation section providing a transport channel between said sections and from the riser into the separation section, in which method the product recovery phase is a liquid phase having a lower density than the aqueous phase, wherein downstream of the riser the reaction mixture comprising the product recovery phase, enriched with produced substance, is separated from the gas that generated or contributed to the upwards motion, wherein said reaction mixture separated from said gas is separated in the separation section into an upper layer comprising the product recovery phase enriched with product substance and a lower layer comprising the aqueous phase, including biocatalyst, wherein product recovery phase enriched with produced substance is recovered from said upper layer, and

wherein aqueous phase, including biocatalyst, from said lower layer is returned to the reaction section.

9. The method according to claim 1, wherein aqueous phase—including, if present, biocatalyst dispersed or dissolved in the aqueous phase—from said lower layer is returned to the reaction section, and wherein a gas is fed, e.g. sparged, into the reaction mixture in the separation section at a position below the interface between the upper and the lower layer.

10. The method according to claim 1, wherein the produced organic substance is selected from the group consisting of hydrocarbons; organic acids; alcohols; ketones; aldehyde; cyclic carboxylic esters; non-cyclic esters; lipids; amines; amino acids; and peptides.

11. The method according to claim 1, wherein the biocatalyst comprises a living organism and the produced substance is secreted into the aqueous phase or wherein the biocatalyst comprises an isolated enzyme or combination of isolated enzymes dispersed or dissolved in the aqueous phase or wherein the biocatalysts is an isolated enzyme or combination of isolated enzymes immobilized on one or more support materials dispersed in the aqueous phase.

12. The method according to claim 1, wherein the biocatalyst comprises a micro-organism selected from the group of bacteria, archaea and fungi, selected from the genera *Pseudomonas, Gluconobacter, Rhodobacter, Clostridium, Escherichia, Paracoccus, Methanococcus, Methanobacterium, Methanocaldococcus, Methanosarcina, Aspergillus, Penicillium, Saccharomyces, Kluyveromyces, Pichia, Candida, Hansenula, Bacillus, Corynebacterium, Blakeslea, Phaffia (Xanthophyllomyces), Yarrowia, Schizosaccharomyces, Zygosaccharomyces* more preferably from the group of *Corynebacterium glutamicum, Escherichia coli, Bacillus subtilis, Bacillus methanolicus, Pseudomonas aeruginosa, Pseudomonas putida, Rhodobacter capsulatus, Rhodobacter sphaeroides, Paracoccus carotinifaciens, Paracoccus zeaxanthinifaciens, Saccharomyces cerevisiae, Saccharomyces pastorianus, Schizosaccharomyces pombe, Aspergillus nidulans, Aspergillus niger, Aspergillus oryzae, Blakeslea trispora, Penicillium chrysogenum, Phaffia rhodozyma (Xanthophyllomyces dendrorhous), Pichia pastoris, Yarrowia lipolytica.*

13. The method according to claim 1, wherein the product recovery phase is a hydrophobic liquid.

14. The method according to claim 1, wherein the providing of the reaction mixture wherein the substance is produced and the separating of the product recovery phase is carried out in a bioreactor system for biocatalytically producing the substance, the bioreactor system comprising an apparatus, said apparatus comprising a reaction compartment, wherein the substance is produced, which reaction compartment is situated in a lower part of the apparatus and a separator compartment, wherein said separation is carried out, the bioreactor system comprising a riser defining a channel at, near or directly above the top of the reaction compartment, which riser is adapted to allow fluid from the reaction compartment to flow upward, a downcomer defining a channel between the outlet side of the riser and the inlet side of the separator compartment, adapted to allow non-gaseous fluid leaving the riser to flow downward into separator compartment, the reaction compartment comprising an agitator, a feed inlet for a substrate for use in the production of the substance, an inlet for the product recovery phase, an inlet for a gas phase, the separator compartment comprising an outlet for product recovery phase, positioned closer to the top of the separator compartment than the outlet end of the downcomer, a recycle provision for recycling fluid containing biocatalyst taken from a part of the separator compartment below the inlet for the gas phase to the separation compartment, and the apparatus having a headspace provided with an outlet for gas phase introduced into the apparatus via the inlets for gas phase, wherein the reaction compartment is positioned below the separator compartment and both compartments are on opposite sides of a partition and the recycle provision comprises one or more openings in the partition, which partition is tilted and wherein one or more openings are present at or near the lowest point of the partition.

15. The method according to claim 14, wherein the tilted partition is at an angle relative to the flow out of the downcomer in the range of 90-120°.

16. The method according to claim 14, wherein the separator compartment comprises an inlet for a gas phase, preferably a micro-bubble sparger which is positioned closer to the bottom of the separator compartment than the outlet end of the downcomer.

17. The method according to claim 14, further comprising a bioreactor vessel having an outlet for a fluid (comprising substrate and optionally biocatalyst and/or produced organic substance) that is connected via a fluid channel with the feed inlet of the reaction compartment of said apparatus.

18. A process for isolating a biocatalytically produced organic substance from a liquid product recovery phase, comprising a first extraction, which comprises the use of the method according to claim 1, wherein the organic substance is extracted from an aqueous reaction medium—wherein the organic substance has been produced in the presence of biocatalyst catalyzing the production of the organic substance—into the liquid product recovery phase, which liquid product recovery phase forms a separate phase when contacted with the reaction medium, which liquid product recovery phase has a boiling point of at least 100° C.;

a separation of the liquid product recovery phase, containing the organic substance from the reaction medium;

a second extraction, which is called a back-extraction, wherein the produced organic substance is extracted from the product recovery phase into a back-extraction liquid, different from the product recovery phase, having a boiling point of less than 100° C.;

a separation of said extraction liquid containing the produced organic substance from the product recovery phase; and an isolation of the organic substance from said extraction liquid.

19. The process according to claim 18, wherein the liquid product recovery phase and the back-extraction liquid are organic liquids, in which process the liquid product recovery phase is an organic liquid selected from the group consisting of fatty acids or esters thereof, waxes, primary alcohols, oils and alkanes having a boiling point of 100° C. or more and/or the back-extraction liquid is an organic liquid selected from the group consisting of alcohols, ethers and esters having a boiling point of less than 100° C.

20. The process according to claim 18, wherein the liquid product recovery phase has an aqueous solubility of less than 85 g/l, preferably of 0 to 1 g/L.

21. The process according to any of the claim 18, wherein the product recovery phase and the back-extraction liquid are brought in contact with each other at a temperature and in a ratio at which they form separate phases and wherein the produced organic substance is extracted from the product recovery phase into the back-extraction liquid, which product recovery phase is essentially insoluble in the back-extraction liquid and/or which back-extraction liquid is essentially insoluble in the product recovery phase; or wherein the product recovery phase and the back-extraction liquid are brought in contact with each other at a temperature and in a ratio at which they form a mixed phase, after which the temperature is changed to induce phase separation, whereby a back-extraction liquid phase is obtained enriched in the biocatalytically produced organic substance.

22. The process according to claim 18, wherein the product is isolated from the back-extraction liquid by distillation, or wherein the product isolated by precipitation, in particular by crystallization, e.g. by reducing the temperature to a temperature at which the organic substance solidifies, whilst the back-extraction liquid remains liquid.

23. The process according to claim 18, wherein the reaction medium is a reaction mixture, wherein the organic substance is produced using a biocatalyst, which reaction mixture comprises an aqueous phase, in which the biocatalyst is dispersed or dissolved, which aqueous phase comprises a substrate for the biocatalyst, and wherein further droplets of the liquid product recovery phase are dispersed in the continuous aqueous phase, into which droplets produced substance migrates; and separating the product recovery phase comprising the produced substance from the aqueous phase and the biocatalyst;

wherein the production of the organic substance and the separation of the product recovery phase are carried out in an apparatus comprising a reaction section, containing the reaction mixture wherein the substance is produced, and a separation section wherein the product recovery phase comprising the produced substance is separated from the aqueous phase.

24. The process according to claim 23, wherein the process comprises a simultaneous production and separation stage, and wherein at least during said simultaneous stage substrate and/or product recovery phase is fed into the reaction section continuously or intermittently, flow conditions in the reaction section are turbulent flow conditions, reaction mixture—of which mixture the product recovery phase comprises the produced substance—is fed continuously or intermittently from the reaction section into the separation section, which fed reaction mixture enters said separation section under essentially laminar flow conditions, in which separation section the product recovery phase is separated from the aqueous phase, under essentially laminar flow conditions or intermittently alternating between laminar flow conditions and no-flow conditions, and product recovery phase, comprising the biocatalytically produced substance, is recovered-continuously or intermittently from the separation section of the apparatus.

\* \* \* \* \*